(12) United States Patent
Freeman et al.

(10) Patent No.: US 11,679,060 B2
(45) Date of Patent: *Jun. 20, 2023

(54) METHOD AND APPARATUS FOR ENHANCEMENT OF CHEST COMPRESSIONS DURING CPR

(71) Applicant: ZOLL Medical Corporation, Chelmsford, MA (US)

(72) Inventors: Gary A. Freeman, Waltham, MA (US); Qing Tan, Somerville, MA (US); Frederick J. Geheb, Danvers, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 196 days.

This patent is subject to a terminal disclaimer.

(21) Appl. No.: 17/064,467

(22) Filed: Oct. 6, 2020

(65) Prior Publication Data

US 2021/0085561 A1    Mar. 25, 2021

Related U.S. Application Data

(63) Continuation of application No. 16/044,650, filed on Jul. 25, 2018, now Pat. No. 10,828,232, which is a
(Continued)

(51) Int. Cl.
*A61B 5/0205* (2006.01)
*A61B 5/11* (2006.01)
(Continued)

(52) U.S. Cl.
CPC ......... *A61H 31/005* (2013.01); *A61B 5/0205* (2013.01); *A61B 5/11* (2013.01);
(Continued)

(58) Field of Classification Search
CPC ......... A61B 5/11; A61B 5/0205; A61B 5/046; A61B 5/04017; A61B 5/721;
(Continued)

(56) References Cited

U.S. PATENT DOCUMENTS 3,865,101 A    2/1975 Saper et al.
4,059,099 A    11/1977 Davis
(Continued)

FOREIGN PATENT DOCUMENTS

EP    1057451    12/2000
EP    1079310    2/2001
(Continued)

OTHER PUBLICATIONS

Aase et al., "Compression Depth Estimation for CPR Qualify Assessment Using DSP on Accelerometer Signals," IEEE Transactions on Biomedical Engineering, vol. 49, No. 3, Mar. 2002.
(Continued)

*Primary Examiner* — Brian T Gedeon
(74) *Attorney, Agent, or Firm* — Mintz Levin Cohn Ferris Glovsky and Popeo, P.C.

(57) ABSTRACT

An apparatus for assisting a rescuer in performing chest compressions during CPR on a victim, the apparatus comprising a pad or other structure configured to be applied to the chest near or at the location at which the rescuer applies force to produce the chest compressions, at least one sensor connected to the pad, the sensor being configured to sense movement of the chest or force applied to the chest, processing circuitry for processing the output of the sensor to determine whether the rescuer is substantially releasing the chest following chest compressions, and at least one prompting element connected to the processing circuitry for pro-
(Continued)

viding the rescuer with information as to whether the chest is being substantially released following chest compressions.

32 Claims, 17 Drawing Sheets

Related U.S. Application Data continuation of application No. 15/371,982, filed on Dec. 7, 2016, now Pat. No. 10,058,477, which is a continuation of application No. 15/246,013, filed on Aug. 24, 2016, now Pat. No. 9,545,359, which is a continuation of application No. 14/512,167, filed on Oct. 10, 2014, now Pat. No. 9,521,978, which is a continuation of application No. 13/872,033, filed on Apr. 26, 2013, now Pat. No. 8,862,228, which is a continuation of application No. 10/786,359, filed on Feb. 24, 2004, now abandoned, which is a continuation-in-part of application No. 10/704,366, filed on Nov. 6, 2003, now Pat. No. 7,220,235.

(51) Int. Cl.
*A61B 5/361* (2021.01)
*A61N 1/04* (2006.01)
*A61N 1/39* (2006.01)
*A61H 31/00* (2006.01)
*A61B 5/00* (2006.01)
*A61B 5/316* (2021.01)
*A61B 5/318* (2021.01)
*A61B 5/1455* (2006.01)

(52) U.S. Cl.
CPC .......... *A61B 5/14551* (2013.01); *A61B 5/316* (2021.01); *A61B 5/318* (2021.01); *A61B 5/361* (2021.01); *A61B 5/4836* (2013.01); *A61B 5/4848* (2013.01); *A61B 5/721* (2013.01); *A61B 5/7207* (2013.01); *A61H 31/006* (2013.01); *A61H 31/007* (2013.01); *A61N 1/046* (2013.01); *A61N 1/0492* (2013.01); *A61N 1/3925* (2013.01); *A61N 1/3987* (2013.01); *A61N 1/3993* (2013.01); *A61H 2201/5043* (2013.01); *A61H 2201/5048* (2013.01); *A61H 2201/5058* (2013.01); *A61H 2201/5079* (2013.01); *A61H 2201/5084* (2013.01); *A61H 2230/04* (2013.01)

(58) Field of Classification Search
CPC ... A61B 5/4848; A61B 5/4836; A61B 5/3987; A61B 5/1455
See application file for complete search history.

(56) References Cited

U.S. PATENT DOCUMENTS

| | | |
|---|---|---|
| 4,088,138 A | 5/1978 | Diack et al. |
| 4,198,963 A | 4/1980 | Barkalow et al. |
| RE30,372 E | 8/1980 | Mirowski et al. |
| 4,296,755 A | 10/1981 | Judell |
| 4,355,634 A | 10/1982 | Kanter |
| 4,588,383 A | 5/1986 | Parker et al. |
| 4,610,254 A | 9/1986 | Morgan et al. |
| 4,619,265 A | 10/1986 | Morgan et al. |
| 4,680,708 A | 7/1987 | Ambos et al. |
| 4,757,821 A | 7/1988 | Snyder |
| 4,781,200 A | 11/1988 | Baker |
| 4,928,674 A | 5/1990 | Halperin et al. |
| 4,947,857 A | 8/1990 | Albert et al. |
| 5,077,667 A | 12/1991 | Brown et al. |
| 5,081,993 A | 1/1992 | Kitney et al. |
| 5,092,341 A | 3/1992 | Kelen |
| 5,109,862 A | 5/1992 | Kelen et al. |
| 5,193,537 A | 3/1993 | Freeman |
| 5,211,179 A | 5/1993 | Haberl et al. |
| 5,247,945 A | 9/1993 | Heinze et al. |
| 5,285,792 A | 2/1994 | Sjoquist et al. |
| 5,330,526 A | 7/1994 | Fincke et al. |
| 5,348,008 A | 9/1994 | Bornn et al. |
| RE34,800 E | 11/1994 | Hutchins |
| 5,365,426 A | 11/1994 | Siegel et al. |
| 5,391,187 A | 2/1995 | Freeman |
| 5,409,010 A | 4/1995 | Beach et al. |
| 5,439,483 A | 8/1995 | Duong-Van |
| 5,454,779 A | 10/1995 | Lurie et al. |
| 5,466,244 A | 11/1995 | Morgan |
| 5,471,991 A | 12/1995 | Shinnar |
| 5,472,453 A | 12/1995 | Alt et al. |
| 5,474,574 A | 12/1995 | Payne et al. |
| 5,496,257 A | 3/1996 | Kelly |
| 5,507,778 A | 4/1996 | Freeman |
| 5,511,553 A | 4/1996 | Segalowitz |
| 5,555,889 A | 9/1996 | Karagueuzian et al. |
| 5,562,710 A | 10/1996 | Olsen et al. |
| 5,589,639 A | 12/1996 | Antonio et al. |
| 5,591,213 A | 1/1997 | Morgan |
| 5,611,815 A | 3/1997 | Cole et al. |
| 5,617,853 A | 4/1997 | Morgan |
| 5,619,265 A | 4/1997 | Suzuki et al. |
| 5,626,140 A | 5/1997 | Feldman et al. |
| 5,645,571 A | 7/1997 | Olson et al. |
| 5,662,690 A | 9/1997 | Cole et al. |
| 5,674,253 A | 10/1997 | Adams et al. |
| 5,683,424 A | 11/1997 | Brown et al. |
| 5,700,281 A | 12/1997 | Brewer et al. |
| 5,735,879 A | 4/1998 | Gliner et al. |
| 5,755,671 A | 5/1998 | Albrecht et al. |
| 5,772,604 A | 6/1998 | Langberg et al. |
| 5,782,888 A | 7/1998 | Sun et al. |
| 5,792,190 A | 8/1998 | Olson et al. |
| 5,853,364 A | 12/1998 | Baker |
| 5,957,856 A | 9/1999 | Weil et al. |
| 5,967,995 A | 10/1999 | Shusterman et al. |
| 6,021,345 A | 2/2000 | Karagueuzian |
| 6,021,349 A | 2/2000 | Arand et al. |
| 6,115,627 A | 9/2000 | Street |
| 6,125,298 A | 9/2000 | Olson et al. |
| 6,125,299 A | 9/2000 | Groenke et al. |
| 6,155,257 A | 12/2000 | Lurie et al. |
| 6,171,257 B1 | 1/2001 | Weil et al. |
| 6,174,295 B1 | 1/2001 | Cantrell et al. |
| 6,178,357 B1 | 1/2001 | Gliner et al. |
| 6,188,928 B1 | 2/2001 | Noren et al. |
| 6,224,562 B1 | 5/2001 | Lurie et al. |
| 6,246,907 B1 | 6/2001 | Lin et al. |
| 6,263,238 B1 | 7/2001 | Brewer et al. |
| 6,289,243 B1 | 9/2001 | Lin et al. |
| 6,306,107 B1 | 10/2001 | Myklebust et al. |
| 6,308,094 B1 | 10/2001 | Shusterman et al. |
| 6,309,695 B1 | 10/2001 | Singh |
| 6,334,070 B1 | 12/2001 | Nova et al. |
| 6,351,671 B1 | 2/2002 | Myklebust et al. |
| 6,360,125 B1 | 3/2002 | Weil et al. |
| 6,390,996 B1 | 5/2002 | Halperin et al. |
| 6,393,316 B1 | 5/2002 | Gillberg et al. |
| 6,397,104 B1 | 5/2002 | Miller et al. |
| 6,418,342 B1 | 7/2002 | Owen et al. |
| 6,427,685 B1 | 8/2002 | Ray, II |
| 6,438,419 B1 | 8/2002 | Callaway et al. |
| 6,466,819 B1 | 10/2002 | Weiss |
| 6,480,734 B1 | 11/2002 | Zhang et al. |
| 6,496,731 B1 | 12/2002 | Lovett |
| 6,572,547 B2 | 6/2003 | Miller et al. |
| 6,575,914 B2 | 6/2003 | Rock et al. |
| 6,597,943 B2 | 7/2003 | Taha et al. |
| 6,622,036 B1 | 9/2003 | Suffin |
| 6,622,042 B1 | 9/2003 | Thacker |
| 6,658,290 B1 | 12/2003 | Lin et al. |
| 6,671,545 B2 | 12/2003 | Fincke |

(56) References Cited

U.S. PATENT DOCUMENTS

| | | |
|---|---|---|
| 6,687,540 B2 | 2/2004 | Marcovecchio |
| 6,697,671 B1 | 2/2004 | Nova et al. |
| 6,766,190 B2 | 7/2004 | Ferek-Petric |
| 6,807,442 B1 | 10/2004 | Myklebust et al. |
| 6,827,695 B2 | 12/2004 | Palazzolo et al. |
| 6,961,612 B2 | 11/2005 | Elghazzawi et al. |
| 6,990,373 B2 | 1/2006 | Jayne et al. |
| 6,993,386 B2 | 1/2006 | Lin et al. |
| 7,006,865 B1 | 2/2006 | Cohen et al. |
| 7,013,176 B2 | 3/2006 | Ding et al. |
| 7,032,596 B2 | 4/2006 | Thompson et al. |
| 7,085,601 B1 | 8/2006 | Bardy et al. |
| 7,089,055 B2 | 8/2006 | Cates et al. |
| 7,220,235 B2 | 5/2007 | Geheb et al. |
| 7,310,553 B2 | 12/2007 | Freeman |
| 7,463,922 B1 | 12/2008 | Snyder et al. |
| 7,488,293 B2 | 2/2009 | Marcovecchio et al. |
| 7,565,194 B2 | 7/2009 | Tan et al. |
| 7,708,683 B2 | 5/2010 | Hadley |
| 7,831,299 B2 | 11/2010 | Tan et al. |
| 8,165,671 B2 | 4/2012 | Freeman et al. |
| 2001/0047140 A1 | 11/2001 | Freeman |
| 2002/0026131 A1 | 2/2002 | Halperin |
| 2002/0055694 A1 | 5/2002 | Halperin et al. |
| 2002/0133197 A1 | 9/2002 | Snyder et al. |
| 2002/0165471 A1 | 11/2002 | Halperin et al. |
| 2002/0165585 A1 | 11/2002 | Dupelle et al. |
| 2002/0193711 A1 | 12/2002 | Halperin et al. |
| 2003/0023277 A1 | 1/2003 | Owen et al. |
| 2003/0055460 A1 | 3/2003 | Owen et al. |
| 2003/0083586 A1 | 5/2003 | Ferek-Petric |
| 2003/0083699 A1 | 5/2003 | Hamilton et al. |
| 2003/0088285 A1 | 5/2003 | Marcovecchio et al. |
| 2003/0130697 A1 | 7/2003 | Halperin et al. |
| 2003/0144699 A1 | 7/2003 | Freeman |
| 2003/0195567 A1 | 10/2003 | Jayne et al. |
| 2004/0044374 A1 | 3/2004 | Weinberg et al. |
| 2004/0049234 A1 | 3/2004 | Morgan et al. |
| 2004/0058305 A1 | 3/2004 | Lurie et al. |
| 2004/0059237 A1 | 3/2004 | Narayan et al. |
| 2004/0082888 A1 | 4/2004 | Palazzolo et al. |
| 2004/0162585 A1 | 8/2004 | Elghazzawi et al. |
| 2004/0171954 A1 | 9/2004 | Holman |
| 2004/0210171 A1 | 10/2004 | Palazzolo et al. |
| 2004/0210172 A1 | 10/2004 | Palazzolo et al. |
| 2004/0215244 A1 | 10/2004 | Marcovecchio et al. |
| 2004/0267324 A1 | 12/2004 | Geheb et al. |
| 2004/0267325 A1 | 12/2004 | Geheb et al. |
| 2005/0021094 A1 | 1/2005 | Ostroff et al. |
| 2005/0027317 A1 | 2/2005 | Langer |
| 2005/0070964 A1 | 3/2005 | Hansen et al. |
| 2005/0101889 A1 | 5/2005 | Freeman et al. |
| 2005/0119706 A1 | 6/2005 | Ideker et al. |
| 2005/0256415 A1 | 11/2005 | Tan et al. |
| 2006/0036292 A1 | 2/2006 | Smith et al. |
| 2006/0116724 A1 | 6/2006 | Snyder |
| 2006/0122648 A1 | 6/2006 | Elghazzawi et al. |
| 2006/0129190 A1 | 6/2006 | Sullivan et al. |
| 2006/0129191 A1 | 6/2006 | Sullivan et al. |
| 2006/0136000 A1 | 6/2006 | Bowers |
| 2006/0155336 A1 | 7/2006 | Heath |
| 2006/0173498 A1 | 8/2006 | Banville et al. |
| 2006/0173499 A1 | 8/2006 | Hampton et al. |
| 2006/0173500 A1 | 8/2006 | Walker et al. |
| 2006/0173501 A1 | 8/2006 | Stickney et al. |
| 2006/0206152 A1 | 9/2006 | Covey et al. |
| 2006/0229679 A1 | 10/2006 | Joo |
| 2006/0259080 A1 | 11/2006 | Vaisnys et al. |
| 2007/0032729 A1 | 2/2007 | Fortin |
| 2007/0032829 A1 | 2/2007 | Ostroff |
| 2007/0179539 A1 | 8/2007 | Degroot et al. |
| 2007/0219588 A1 | 9/2007 | Freeman |
| 2007/0233197 A1 | 10/2007 | Jung et al. |
| 2008/0009908 A1 | 1/2008 | Parascandola et al. |
| 2008/0015645 A1 | 1/2008 | Kelly et al. |
| 2008/0033494 A1 | 2/2008 | Swerdlow |
| 2008/0033495 A1 | 2/2008 | Kumar |
| 2008/0046015 A1 | 2/2008 | Freeman et al. |

FOREIGN PATENT DOCUMENTS

| | | |
|---|---|---|
| EP | 1491176 | 12/2004 |
| EP | 2532340 | 12/2012 |
| GB | 9713345.8 | 6/1997 |
| GB | 2314648 | 1/1998 |
| JP | 2001-104259 | 4/2001 |
| JP | 2003-521355 | 7/2003 |
| WO | WO 1997/24062 | 7/1997 |
| WO | WO1998/30282 | 7/1998 |
| WO | WO1999/24114 | 5/1999 |
| WO | WO1999/25306 | 5/1999 |
| WO | WO2000/027464 | 5/2000 |
| WO | WO2001/56652 | 8/2001 |
| WO | WO2001/66182 | 9/2001 |
| WO | WO2002/15836 | 2/2002 |
| WO | WO2003/009895 | 2/2003 |
| WO | WO2004/054656 | 7/2004 |
| WO | WO2005/021089 | 3/2005 |
| WO | WO2003/020364 | 3/2013 |

OTHER PUBLICATIONS

Aase et al., "CPR Artifact Removal from Human ECG Using Optimal Multichannel Filtering", IEEE Transactions on Biomedical Engineering, vol. 47:11, pp. 1440-1449 (2000).

Afonso et al., "Detecting Ventricular Fibrillation", IEEE Engineering In Medicine and Biology, vol. 14:2, pp. 152-159 (1995).

Al-Fahoum et al., "Combined wavelet transformation and radial basis neural networks for classifying life-threatening cardiac arrhythmias", Medical & Biological Engineering & Computing, vol. 37:5, pp. 566-573 (1999).

Amann et al., Reliability of Fibrillation Detection Algorithms In Automatic External Defibrillators (AEDs), Dept. of Anaesthesia and Intensive Care Medicine, Leopold-Franzens-Universitat Innsbruck, Anichstr. 35, A-6020 Innsbruck, Austria, Dept. of Computer Science, Applied Mathematics Group, FH-Vorarlberg, Achstr. 1, A-6850 Dornbirn, Austria. At the top of the paper I have is the following: Jahrestaguug der Osterreichischen Deutschen und Schweizerischen Gesellschaft fur Biomedizimische Technik Sep. 2003.

American Red Cross—Adult CPR/AED Training—Workplace Programs, http://www.redcross.org/hss/cpraed.html, printed from Internet May 14, 1999.

Barro et al., "Algorithmic sequential decision-making in the frequency domain for life threatening ventricular arrhythmias and imitative artifacts: a diagnostic system", J. Biomed. Eng., vol. 11:4, pp. 320-328 (1989).

Botsivaly et al., "Evaluation of a new technique for the Detection of Ventricular Fibrillation and Ventricular Tachycardia", Procs of the 22nd Ann EMBS Int Conf, Chicago, IL (2000).

Callaway et al., "Scaling exponent predicts defibrillation success for out-of-hospital ventricular fibrillation cardiac arrest," Circulation 103(12):1656-1661 (2001).

Callaway et al., "Ventricular Fibrillation Waveform Predicts Defibrillation Success by Automatic External Defibrillators", Academic Emergency Medicine, vol. 7:5, pp. 1-2 (2000).

Cardiac Science Brochure, Analysis Algorithm Overview, Powerheart® AED Automated External Defibrillator with RHYTHMx® Technology (no date).

Clayton et al., "Comparison of four techniques for recognition of ventricular fibrillation from the surface ECG", Medical & Biological Engineering & Computing, vol. 31:2, pp. 111-117 (1993).

Efestol et al., "Probability of successful defibrillation as a monitor during CPR in out-of-hospital cardiac arrested patients," Resuscitation 48(3):245-254 (2001).

Eftestol et al., "Effects of Interrupting Precordial Compressions on the Calculated Probability of Defibrillation Success During Out-of-Hospital Cardiac Arrest," Circulation, 105, 2270-2273, (2002).

(56) References Cited

OTHER PUBLICATIONS

Eftestol et al., "Predicting Outcome of Defibrillation by Spectral Characterization and Nonparametric Classification of Ventricular Fibrillation in Patients With Out-of-Hospital Cardiac Arrest", Circulation, 102:1523-1529 (2000).
Fitzgibbon et al., "Determination of the noise source in the electrocardiogram during cardiopulmonary resuscitation", Crit Care Med, vol. 30:4, pp. S148-S152 (2002).
Flewelling, Nellcor Incorporated, Noninvasive Optical Monitoring, Chap. 88, pp. 1346-1353. CRC Press, Inc., 1995.
Force Sensing Resistors—An Overview of the Technology, FSR Integration Guide & Evaluation Parts Catalog with Suggested Electrical Interfaces (no date).
Ge et al., "Cardiac arrhythmia classification using autoregressive modeling", Biomed Eng. Online, pp. 13, (2002).
Geheb, Frederick J., "A System for the Determination of Ventricular Tachycardia or Ventricular Fibrillation during Cardio-Pulmonary Resuscitation", 2 pages (Apr. 2002).
Gruben et al., "System for Mechanical Measurements During Cardiopulmonary Resuscitation in Humans," IEEE Transactions on Biomedical Engineering, vol. 37, No. 2, Feb. 1990.
Haykin, Adaptive Filter Theory, Third Edition, Upper Saddle River, NJ, USA, Prentice-Hall, 1996.
Heartstream—The Background Behind Our Technology, http://www.heartstream.com/techbk.htm, printed from Internet Jun. 25, 1999.
Husoy et al., "Removal of Cardiopulmonary Resuscitation Artifacts From Human ECG Using an Efficient Matching Pursuit-Like Algorithm", IEEE Transactions on Biomedical Engineering, vol. 49:11, pp. 1287-1298 (2002).
Johnston et al., "The Potential Use of Impedance . . . Automated External Defibrillators." Jour. of the Amer, Coll. of Cardiology, 1995, vol. 25, Issue 2, Supplement 1, p. 211A.
Khadra et al., "Detection of life-threatening cardiac arrhythmias using the wavelet transformation", Medical & Biological Engineering & Computing, vol. 35:5, pp. 626-632 (1997).
Kuo et al., "Computer Detection of Ventricular Fibrillation", Computers in Cardiology, pp. 347-349 (Sep. 1978).
Langhelle et al. "Reducing CPR Artifacts in Ventricular Fibrillation in Vitro," Resuscitation. Mar; 48(3):279-91 (2001).
Lightfoot et al., "Dynamic nature of electrocardiographic waveform predicts rescue shock outcome in porcine ventricular fibrillation," Ann. Emerg. Med. 42(2):230-41 (Aug. 2003).
Menegazzi et al., "Immediate defibrillation versus interventions first in a swine model of prolonged ventricular fibrillation", Resuscitation, vol. 59, pp. 261-270 (2003).
Menegazzi et al., "Ventricular Fibrillation Scaling Exponent Can Guide Timing of Defibrillation and Other Therapies", Circulation, 109:926-931 (Feb. 2004).
Noc et al., "Electrocardiograph Prediction . . . Cardiac Resuscitation," Critical Care Medicine, Williams and Wilkins Co., Baltimore, vol. 27, No. 4, pp. 708-714 (Apr. 1, 1999).
Nygards et al., "Recognition of Ventricular Fibrillation Utilizing The Power Spectrum of The ECG", Computers in Cardiology, pp. 393-397 (1997).
Patterson, "Impedance cardiography: What is the source of the signal?", Int. Conf. on Elec. Bioimpedance, Journal of Physics: Conf. Series 224 (2010).
Pinchak et al., "Chest wall acceleration . . . resuscitation," Critical Care Medicine, vol. 16, No. 2, pp. 151-160, 1988.
Povoas et al., "Predicting the success of defibrillation by electrocardiographic analysis," Resuscitation 53(1):77-82 (2002).
Sato et al., "Adverse effects of interrupting precordial compression during cardiopulmonary resuscitation," Critical Care Medicine, vol. 25(5), 733-736 (1997).
Sherman et al., "Ventricular fibrillation exhibits dynamical properties and self-similarity", Resuscitation, vol. 47, pp. 163-173 (2000).
Strohmenger, "Kammerflimmern/-flattern: Defibrillationserfolg?", Notfall & Rettungsmedizin, vol. 6, pp. 22-26 (Feb. 1, 2003) (English Abstract).
U.S. Appl. No. 10/370,036 (Elghazzawi et al., CPR Sensitive ECG Analysis in an Automatic External Defibrillator).
U.S. Appl. No. 10/421,652 (Marcovecchio, Optical Pulse Sensor for External Defibrillator).
U.S. Appl. No. 10/441,933 (Marcovecchio, Processing Pulse Signal in Conjunction with ECG Signal) (0132001).
Wang et al., "Effects of Biphasic vs Monophasic Defibrillation on the Scaling Exponent in a Swine Model of Prolonged Ventricular Fibrillation", Academic Emergency Medicine, vol. 8:8, pp. 771-780 (2001).
Watson et al., "A novel wavelet transform based analysis reveals hidden structure in ventricular fibrillation", Resuscitation, vol. 43:2, pp. 121-127 (2000).
Yoji et al., "Adverse effects of interrupting precordial compression during cardiopulmonary resuscitation", Critical Care Medicine, vol. 25:5, 733-736 (1997).
Yu et al., "Adverse Outcomes of Interrupted Precordial Compression During Automated Defibrillation", Circulation, pp. 368-372 (Jul. 2002).

METHOD AND APPARATUS FOR ENHANCEMENT OF CHEST COMPRESSIONS DURING CPR

CROSS-REFERENCE TO RELATED APPLICATIONS

This application is a continuation application of and claims priority to U.S. application Ser. No. 16/044,650, filed Jul. 25, 2018, which is a continuation application of and claims priority to U.S. application Ser. No. 15/371,982, filed Dec. 7, 2016, now U.S. Pat. No. 10,058,477, which application is a continuation application of and claims priority to U.S. application Ser. No. 15/246,013, filed Aug. 24, 2016, now U.S. Pat. No. 9,545,359, which application is a continuation application of and claims priority to U.S. application Ser. No. 14/512,167, filed Oct. 10, 2014, now U.S. Pat. No. 9,521,978, which application is a continuation application of and claims priority to U.S. application Ser. No. 13/872,033, filed Apr. 26, 2013, now U.S. Pat. No. 8,862,228, which application is a continuation application of and claims priority to U.S. application Ser. No. 10/786,359, filed Feb. 24, 2004, now abandoned, which application is a continuation-in-part of and claims priority to U.S. application Ser. No. 10/704,366, filed on Nov. 6, 2003, now U.S. Pat. No. 7,220,235. All are hereby incorporated by reference.

TECHNICAL FIELD

This invention relates to the devices for assisting cardiac resuscitation.

BACKGROUND

This invention relates to the field of cardiac resuscitation, and in particular to devices for assisting rescuers in performing chest compression during cardio-pulmonary resuscitation (CPR). Chest compression during CPR is used to mechanically support circulation in subjects with cardiac arrest, by maintaining blood circulation and oxygen delivery until the heart is restarted. The victim's chest is compressed by the rescuer, ideally at a rate and depth of compression in accordance with medical guidelines, e.g., the American Heart Association (AHA) guidelines. One key step for creating blood flow through the heart is to release the chest adequately after each chest compression. The chest should be released sufficiently to create a negative pressure in the chest, to facilitate venous filling of the heart and increased blood flow upon the next chest compression. If the chest is not released adequately, a positive thoracic pressure will remain which will hinder venous return and right atrial filling. Other key CPR parameters are maximal velocity of compression, compression depth, and average velocity. Compression depth and average velocity, together, provide good indication of potential blood flow volume. Maximal velocity of compression is an important factor in proper mitral valve closure and higher blood flow volume.

Sensors have been suggested for detecting the depth of chest compression. An accelerometer (with its output integrated to estimate depth) was disclosed, for example, in Freeman U.S. application Ser. No. 09/794,320, U.S. Pat. Nos. 6,306,107 and 6,390,996. Force (pressure) sensors were disclosed, for example, in Groenke U.S. Pat. No. 6,125,299. Force sensors provided no way of determining absolute displacement, as the compliance of the thoracic cage varies considerably from person to person. Accelerometers do not provide an indication of whether or not the chest is being released. They calculate displacement by double integration, which can result in a significant DC offset. U.S. Pat. No. 6,306,107 attempted to address the DC offset problem by incorporating a force sensor as a switch to indicate onset and conclusion of compression. The prior art has also employed mechanical pressure gauges to indicate to the rescuer the amount of force or pressure being applied to the chest. But these prior art uses of an accelerometer and/or force sensor have not provided a good solution to providing the rescuer with useful feedback as to whether the chest has been sufficiently released. Differences in compliance of the thoracic cage from one individual to another means that each individual will generally be able to support different amounts of force on the sternum without significant displacement occurring.

Increasingly, automated external defibrillators (AEDs) are used by rescuers treating victims of cardiac arrest for the delivery of defibrillatory shocks with the minimum of delay. The algorithms contained in the currently-available AEDs call for 'hands off' periods during which electrocardiographic (ECG) analysis is performed by the device and the rescuer withholds compressions. Compressions must be withheld because the accuracy of current rhythm analysis algorithms in AEDs is severely degraded by the artifact induced by the chest compressions. These AEDs also call for the rescuer to check for pulse or for signs of circulation during which time no compressions are performed. It has been shown in several studies that interruptions in the performance of chest compressions of as short a time as 20 seconds can dramatically reduce the probability of the return of spontaneous circulation (ROSC), a key survival measure. Other studies have also shown that the minimum amount of time required for the 'hands off' period is 20 seconds. There is therefore a need for the ability of AEDs to perform rhythm analysis while the rescuer continues with the chest compressions uninterrupted.

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. The term basic life support (BLS) involves all the following elements: initial assessment; airway maintenance; expired air ventilation (rescue breathing); and chest compression. When all three (airway breathing, and circulation, including chest compressions) are combined, the term cardiopulmonary resuscitation (CPR) is used.

Current automated ECG rhythm analysis methods interrupt cardiopulmonary resuscitation (CPR) to avoid artifacts in the ECG resulting from chest compressions. Long interruptions of CPR have been shown to result in higher failure rate of resuscitation. Studies have reported that the discontinuation of precordial compression can significantly reduce the recovery rate of spontaneous circulation and the 24-hour survival rate. Y. Sato, M H. Weil, S. Sun, W. Tang, J. Xie, M. Noc, and J. Bisera, Adverse effects of interrupting precordial compression during cardiopulmonary resuscitation, Critical Care Medicine, Vol. 25(5), 733-736 (1997). Yu et al., 2002. Circulation, 106, 368-372 (2002), T. Eftestol, K. Sunde, and P A. Steen, Effects of Interrupting Precordial Compressions on the Calculated Probability of Defibrillation Success During Out-of-Hospital Cardiac Arrest, Circulation, 105, 2270-2273, (2002).

Management of breathing is another important aspect of the CPR process. Typical methods of monitoring breathing employ some form of impedance pneumography which measure and track changes in the transthoracic impedance of the patient. Currently, however, chest compressions result in significant artifact on the impedance signals, resulting in impedance-based pneumographic techniques as unreliable indicators of lung volume during chest compressions.

Adaptive filters have been attempted as a way of removing chest-compression artifacts in the ECG signal. S O. Aase, T. Eftestol, J H. Husoy, K. Sunde, and P A. Steen, CPR Artifact Removal from Human ECG Using Optimal Multichannel Filtering, IEEE Transactions on Biomedical Engineering, Vol. 47, 1440-1449, (2000). A. Langhelle, T. Eftestol, H. Myklebust, M. Eriksen, B T. Holten, P A. Steen, Reducing CPR Artifacts in Ventricular Fibrillation in Vitro. Resuscitation. March; 48(3):279-91 (2001). JH. Husoy, J. Eilevstjonn, T. Eftestol, S O. Aase, H Myklebust, and PA. Steen, Removal of Cardiopulmonary Resuscitation Artifacts from Human ECG Using an Efficient Matching Pursuit-Like Algorithm, IEEE Transactions on Biomedical Engineering, Vol 49, 1287-1298, (2002). H R. Halperin, and R D. Berger, CPR Chest Compression Monitor, U.S. Pat. No. 6,390,996 (2002). Aase et al. (2000) and Langhelle et al. (2001) used the compression depth and thorax impedance as reference signals for their adaptive filter. Husoy et al. (2002) extended this study by using a matching pursuit iteration to reduce the computational complexity; however, their results are usually computationally intensive, such as involving the calculation of a high order inverse filter. Halperin et al. (2002) proposed a frequency-domain approach using the auto- and the cross-spectrum of the signals and a time-domain approach using a recursive least square method for adaptive filtering the ECG signal. In both approaches, intensive computations are required.

There are numerous references available on adaptive filters. E.g., S. Haykin, Adaptive Filter Theory, Third Edition, Upper Saddle River, N.J., USA. Prentice-Hall, 1996

SUMMARY

In a first aspect, the invention features an apparatus for assisting a rescuer in performing chest compressions during CPR on a victim, the apparatus comprising a pad or other structure configured to be applied to the chest near or at the location at which the rescuer applies force to produce the chest compressions, at least one sensor connected to the pad, the sensor being configured to sense movement of the chest or force applied to the chest, processing circuitry for processing the output of the sensor to determine whether the rescuer is substantially releasing the chest following chest compressions, and at least one prompting element connected to the processing circuitry for providing the rescuer with information as to whether the chest is being substantially released following chest compressions.

Preferred implementations of this aspect of the invention may incorporate one or more of the following. The pad or other structure may be a pad to which force is applied by rescuer. The sensor may include an accelerometer. The sensor may include a force (or pressure) sensor. The sensor may include a velocity sensor. The sensor may include both a force (or pressure) sensor and an accelerometer or velocity sensor. The prompting device may include a speaker for delivering an audible message to the rescuer. The prompting device may include a display for delivering a visual message to the rescuer. The apparatus may be part of an external defibrillator. The external defibrillator may be an AED. The processing circuitry may include a digital processor executing software. Determining whether the rescuer is substantially releasing the chest may comprise analyzing motion of the chest. Analyzing motion of the chest may comprise analyzing features or the shape of a waveform representing chest motion. The apparatus may comprise both a sensor to sense movement of the chest and a sensor to sense force applied to the chest, and the processing circuitry may use outputs of both sensors to provide information representative of chest compliance. The information representative of chest compliance may be used to determine a level of applied pressure/force that corresponds to a substantial release of the chest.

In a second aspect, the invention features an apparatus for assisting a rescuer in performing chest compressions during CPR on a victim, the apparatus comprising a pad or other structure configured to be applied to the chest near or at the location at which the rescuer applies force to produce the chest compressions, and at least one velocity sensor connected to the pad, the velocity sensor being configured to sense the velocity of movement of the chest.

Preferred implementations of this aspect of the invention may incorporate one or more of the following. The apparatus may further comprise processing circuitry for processing the output of the velocity sensor to estimate the displacement of the chest. The processing circuitry may have the capability to integrate an output of the velocity sensor. The velocity sensor may be configured to be located approximately adjacent to the location at which the body is compressed. The velocity sensor may be configured to be positioned to sense the relative velocity between opposite surfaces of the chest. The velocity sensor may comprise a conductor and a magnet, and velocity may be sensed by sensing the current induced in the conductor by relative motion between the conductor and the magnet. The magnet may comprise one of a permanent magnet and an electromagnet. The conductor and magnet may be positioned on opposite surfaces of the chest. The conductor may comprise a coil that is unitary with a defibrillation electrode pad. The conductor and magnet each may comprise a coil that is unitary with a defibrillation electrode pad. The magnet may comprise an electromagnet and the electromagnet may produce a magnetic field that oscillates at a frequency greater than 1 KHz, and may further comprise coil detection circuitry to which the coil is connected, wherein the coil detection circuitry may be capable of synchronously demodulating the detected signal to reduce susceptibility to drift and noise. The apparatus may further comprise circuitry for acquiring ECG signals from the victim, and the processing circuitry may have the capability to process the output of the velocity sensor and the ECG signals to reduce ECG artifacts from chest compressions by use of velocity sensor output.

In a third aspect, the invention features an apparatus for assisting a rescuer in performing chest compressions during CPR on a victim, the apparatus comprising a pad or other structure configured to be applied to the chest near or at the location at which the rescuer applies force to produce the chest compressions, at least one motion sensor connected to the pad, the motion sensor being configured to sense movement of the chest, processing circuitry for processing the output of the motion sensor to estimate the maximum velocity of compression of the chest, and at least one prompting device connected to the processing circuitry for providing the rescuer with information representative of the maximum velocity of compression. In preferred implementations of this aspect of the invention, the motion sensor may comprise a velocity sensor.

In a fourth aspect, the invention features a method of determining chest compression during CPR, the method comprising applying a motion sensor to the chest of a patient at a location near or at the location at which a rescuer applies force to produce chest compressions, determining chest displacement from analysis of features of the motion waveform produced by the motion sensor.

Preferred implementations of this aspect of the invention may incorporate one or more of the following. The motion sensor may be a velocity sensor. The motion sensor may be an accelerometer. The method may further comprise deciding from the analysis of features of the acceleration waveform whether or not a rescuer has sufficiently released the patient's chest. The method may further comprise processing the output of the accelerometer to provide velocity and acceleration waveforms. The method may further comprise processing the output of the accelerometer to provide velocity and acceleration waveforms, and analyzing the velocity and acceleration waveforms to determine whether or not a rescuer has sufficiently released the patient's chest. The analysis of velocity waveforms may include determining the maximal velocity of compression. Determining chest displacement from analysis of features may comprise determining onset and completion times for a compression cycle from the features of the waveforms. Determining chest displacement may further comprise integrating the acceleration waveform over a time segment defined by the onset and completion times. The method may further comprise analyzing the features of the upstroke portion of the waveforms to determine whether there has been sufficient release of the chest. The method may further comprise prompting a rescuer based as to whether compressions are within desired limits on compression depth and compression release. The prompts to the rescuer may be based on multi-cycle trends, so that they are not immediately influenced by the rescuer taking a brief break in the application of CPR. The method may further comprise determining chest compliance, and using the determined chest compliance to adjust the level of pressure/force that the rescuer is permitted to apply at the end of a compression stroke without being prompted as to insufficiently releasing the chest. The features determined from the waveforms may include one or more of the following: width, amplitude, area, center of mass, skewness, height/width ratio, TAR, TAMPR and TWR. The features may be used to make a decision as to whether the chest of the victim has been sufficiently released. Decisions may be made using either standard decision logic, fuzzy-logic decision methodology, or statistical estimation.

In a fifth aspect, the invention features a method of analyzing ECG signals during application of CPR, the method comprising detecting ECG signals during application of chest compressions, detecting the output of a sensor from which information on the velocity of chest compressions can be determined, and using the information on the velocity to reduce at least one signal artifact in the ECG signal resulting from the chest compressions.

Preferred implementations of this aspect of the invention may incorporate one or more of the following. The sensor may be a velocity sensor, and the information on the velocity may be determined from the velocity sensor. The sensor may be an accelerometer, and the information on the velocity may be determined from integration of the output of the accelerometer. Using the information on the velocity to reduce at least one signal artifact in the ECG signal may comprise time aligning the ECG signals with the velocity. Using the information on the velocity to reduce at least one signal artifact in the ECG signal may comprise an adaptive filter that is adjusted to remove chest compression artifacts. Using the information on the velocity to reduce at least one signal artifact in the ECG signal may comprise feed forward active noise cancellation. Using the information on the velocity to reduce at least one signal artifact in the ECG signal may comprise determining a cutoff frequency for a filter that separates the ECG signal from chest compression artifacts.

In a sixth aspect, the invention features an apparatus for assisting a rescuer in performing chest compressions during CPR on a victim, the apparatus comprising a pad or other structure configured to be applied to the chest near or at the location at which the rescuer applies force to produce the chest compressions, at least one motion sensor connected to the pad, the motion sensor being configured to sense movement of the chest, at least one force (or pressure) sensor connected to the pad, the force sensor being configured to sense force applied to the chest, and processing circuitry for processing the output of the motion sensor and force sensor to estimate the compliance of the chest.

Preferred implementations of this aspect of the invention may incorporate one or more of the following. The estimated compliance and the output of the force sensor may be used to determine the depth of compression of the chest. The motion sensor may be an accelerometer, and the output of the accelerometer may be used primarily for estimating chest compliance, and compression depth during CPR may be estimated by using the estimated compliance to convert the output of the force sensor into estimated compression depth. The output of the accelerometer may be used during limited time intervals for estimating chest compliance, and outside of those limited time intervals chest compression may be determined from the estimated compliance and the output of the force sensor without substantial use of the output of the accelerometer. The estimated compliance and the output of the force sensor may be used to determine whether the chest has been substantially released.

In a seventh aspect, the invention features an apparatus for assisting a rescuer in performing chest compressions during CPR on a victim, the apparatus comprising a pad or other structure configured to be applied to the chest near or at the location at which the rescuer applies force to produce the chest compressions, at least one bistable mechanical element that when depressed provides tactile feedback to the hand of the rescuer upon the start of a compression and at the end of a compression.

Preferred implementations of this aspect of the invention may incorporate one or more of the following. The mechanical element may comprise a dome that collapses under pressure and returns to a dome shape on release of pressure. The bistable mechanical element may further provide audible feedback at least at the end of a compression. The tactile feedback at the end of a compression may occur at approximately an applied force corresponding to substantial release of the chest, so that the tactile feedback serves as feedback to the rescuer that the chest has been substantially released.

The invention provides numerous advantages. It provides a more accurate and detailed measure of compressions during CPR, e.g., by analyzing such compression/decompression cycle parameters as compression velocity and completeness of decompression release. And features of the velocity and acceleration waveforms may be analyzed to maximize CPR performance. E.g., the invention permits analysis of maximal velocity of compression, which is an important factor in proper mitral valve closure and higher blood flow volume.

The invention may obviate the need for a secondary information channel, e.g., a force sensor, to provide the accuracy necessary for the use of acceleration to accurately measure displacement. The invention includes new methods for the analysis of the acceleration waveform that allow for decreased offset drift and improved displacement accuracy. The methods also provide for the ability to determine parameters relating to the quality of the compression/decompression cycle by morphological analysis of the acceleration and velocity waveform. Multiple parameters may be determined via the analysis and then combined in making a decision regarding chest release or other generalized descriptor of compression/decompression quality. The methods used may include standard decision logic (e.g., IF-THEN-ELSE) or may involve methods such as fuzzy-logic decision methodology or statistical estimation such as Bayesian methods.

Direct physiological measurements of perfusion and oxygenation, such as end-tidal carbon dioxide (EtCO2) and pulse oximetry, can provide additional feedback to the CPR control algorithm.

By determining chest compliance, some implementations of the invention overcome the difficulty of using a pressure/force sensor for determining the onset and release of compression. The compliance of the thoracic cage varies from person to person, and therefore each individual will generally be able to support different amounts of force on the sternum without any displacement occurring. In some implementations of the invention, compliance is estimated from measurements of force (or pressure) and chest motion during compressions. The estimated compliance can be used to adapt the chest-released force threshold to patients with differing chest compliance. Without adapting the threshold to the victim's chest compliance, the chest-released force threshold tends to have to be set quite low, to assure substantial release even on patients with large compliance. This can result in requiring the rescuer to release nearly all force from the chest, interfering with the process of CPR itself and confusing the rescuer with what appears to be irrelevant and interfering commands.

Using a velocity sensor (as proposed with some aspects of the invention), can provide a more accurate and less noise sensitive measure for determining displacement. It requires only one integration to calculate displacement from velocity, thus reducing offset error, and it requires only one differentiation to calculate acceleration thus reducing high frequency noise susceptibility. Additionally, velocity in this implementation is a differential configuration that measures relative velocity between the front and back of the thorax, unlike acceleration which is inertial and whose motion is relative to the Earth. Differential velocity measurement provides a significantly improved performance during patient transport such as in an ambulance or on an airplane. In fact, the vibration and motion may make the acceleration for the most part unusable in these situations.

Magnetic induction may be used to generate a voltage proportional to the relative velocity between a magnet and coil. The magnet may take the form of a permanent magnet, but preferably it is an electromagnet. The use of an electromagnet serves two main purposes: it can be used to calibrate the setup after the electrodes have been applied to the patient, and it can be used to provide a synchronous modulation/demodulation of the signal to improve accuracy and minimize susceptibility to noise and artifact.

The magnetic pickup and induction coils may be incorporated into defibrillation pads. One defibrillation pad can be placed on the left thorax and another defibrillation pad can be placed on the victim's back in the left scapular area. These are excellent locations for defibrillation and provide a good placement to generate magnetic flux changes proportional to sternal displacement. The coils can incorporated directly into the outer edge of each of the defibrillation electrodes. Alternatively, if the desired electrode position is anterior/anterior with both electrodes on the front of the chest, a separate backboard panel may be supplied which is placed under the patient and contains the receiving coil.

The invention's use of velocity sensor, which may make it possible to perform ECG analysis without a "hands off" period provides improved filtering and rhythm analysis.

In general the invention features a method of analyzing a physiological (e.g., an ECG) signal during application of chest compressions. The method includes acquiring a physiological signal during application of chest compressions; acquiring the output of a sensor from which information on the velocity of chest compressions can be determined; and using the information on the velocity to reduce at least one signal artifact in the physiological signal resulting from the chest compressions.

Preferred implementations of the invention may incorporate one or more of the following: The physiological signal may be any of a variety of physiological signals, including an ECG signal, an IPG signal, an ICG signal, or a pulse oximetry signal. The sensor may be a velocity sensor, and the information on the velocity may be determined from the velocity sensor. The sensor may be an accelerometer, and the information on the velocity may be determined from integration of the output of the accelerometer. Using the information on the velocity to reduce at least one signal artifact in the physiological signal may comprise time aligning the physiological signal with the velocity. Using the information on the velocity to reduce at least one signal artifact in the physiological signal may comprise using an adaptive filter that may be adjusted to remove chest compression artifacts. The method may include a ventricular fibrillation detection algorithm for processing the physiological signal with reduced artifact to estimate whether a ventricular fibrillation may be present. The method may include a preprocessing step that detects when chest compressions are applied and automatically initiates the adaptive filter. The method may include enabling delivery of a defibrillation shock if the algorithm estimates that ventricular fibrillation is present. A difference signal may be produced, the difference signal being representative of the difference between the physiological signal fed into the adaptive filter and the physiological signal after artifact reduction by the adaptive filter. The difference signal may provide a measure of the amount of artifact in the physiological signal. The difference signal may be used to modify the subsequent processing of the physiological signal. If the difference signal indicates that the amount of artifact exceeds a first threshold, the ventricular fibrillation detection algorithm may be modified to make it more resistant to being influenced by the artifact. If the difference signal indicates that the amount of artifact exceeds a second threshold higher than the first threshold, use of the ventricular defibrillation detection algorithm may be suspended. Spectral analysis may be performed on the difference signal, and adjustments may be made to filtering of the physiological signal based on the outcome of the spectral analysis. The velocity signal may undergo a normalization pre-processing prior to being fed to an adaptive filter. The adaptive filter may include an FIR filter. The adaptive filter may include a zero-th order filter. The adaptive filter may have coefficients that are dynamically controlled by an estimate of the physiological signal. The adaptive filter may have the capability of being automatically reset when the difference between the filter output and the measured physiological signal is beyond a threshold. The automatic reset may be capable of dynamically changing the step size and thus improving the relationship of convergence and stability of the filter. A time-aligning process may be performed on the physiological and velocity signals, wherein the time aligning process aligns the two signals relative to the compressions. The method may include adaptive filtering of the output of the time aligning process, wherein the adaptive filtering reduces the error between the physiological and velocity signals. The adaptive filter may include a Kalman filter. The adaptive filter may employ adaptive equalization.

Among the many advantages of the invention (some of which may be achieved only in some of its various implementations) are the following:

This invention provides excellent techniques for (a) adaptively removing the artifacts induced by CPR in an ECG signal, (b) enhancing an ECG signal for monitoring, and (c) increasing the reliability of ECG rhythm advisory algorithms.

As part of a rhythm advisory algorithm, various implementations of the invention could be incorporated in an ECG monitor, an external defibrillator, an ECG rhythm classifier, or a ventricular arrhythmia detector.

The invention makes it possible to continue performing CPR while ECG data is collected for an ECG rhythm advisory algorithm. This can enhance the result of CPR, leading, for example, to an increase in the success rate of resuscitation.

The invention can also provide a "cleansed" ECG signal output for display to the user of a defibrillator.

The invention also provides for the first time a means of measuring lung volume during chest compressions by impedance-based methods. The method may also be used to filter other physiological signals corrupted by compression-induced artifact, such as impedance cardiography and pulse oximetry.

This invention demonstrates excellent performance at removing the CPR artifact with a zero-th order FIR filter, thus making some implementations of the invention much simpler and faster than the adaptive-filter structures proposed in the prior art.

Pre-processing of the reference signal and an automatic-reset feature make it possible for some implementations of the invention to use a relatively large step size for adaptation, thus making convergence faster and more stable.

Some implementations of the invention achieve excellent performance in CPR-artifact removal at reduced computational cost.

Other features and advantages of the invention will be apparent from the following detailed description and drawings, and from the claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
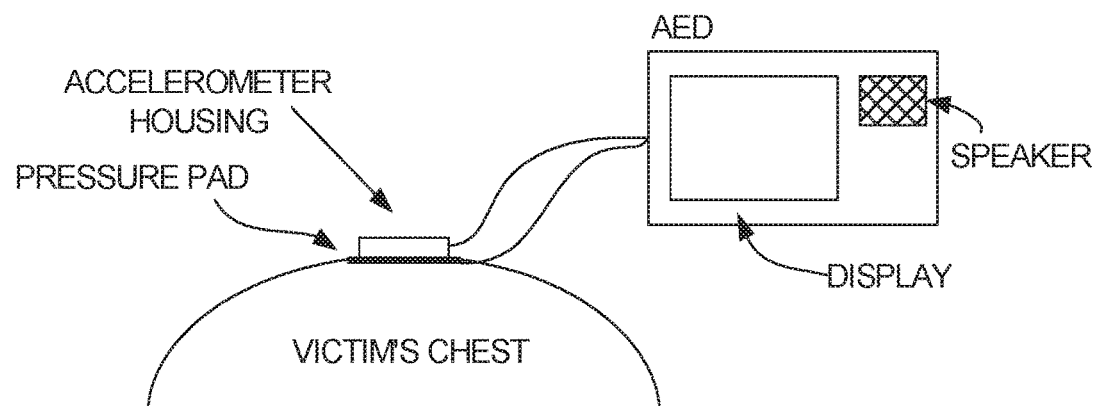
FIG. 1 is a diagram of one implementation including an AED and an accelerometer and pressure/force sensor built into a chest-mounted pad.

FIG. 1 shows a schematic of a preferred implementation. This implementation includes an accelerometer (and accelerometer housing), force sensor built into a pressure pad, and an AED which is electrically connected to the accelerometer and force sensor and contains a display and/or speaker for user feedback. The pressure pad provides the structural member on which the accelerometer (and housing) is supported. Neither the accelerometer nor force sensor of the pad are essential to detecting chest release, as other sensors can be used. The force sensor can measure force or pressure.

The accelerometer housing can be shaped similar to a hockey puck and can rest either directly on the patient's sternum or on the pad or other structural member. Preferably the accelerometer is positioned to be over the victim's sternum in the position recommended for chest compressions. A force sensor can be placed below (as shown) or above the accelerometer housing. The rescuer presses on the accelerometer housing (or pressure pad) to perform chest compressions. The accelerometer senses the motion of the chest during CPR and the force sensor measures the force or pressure applied. The AED supplies power to the sensors and digitizes the electrical signals coming from the accelerometer and force sensor. Based on previous calibrations of the sensors, the accelerometer signal is integrated to determine the housing displacement, and the output of the force sensor is converted to standard pressure or force units.

Figure 2:
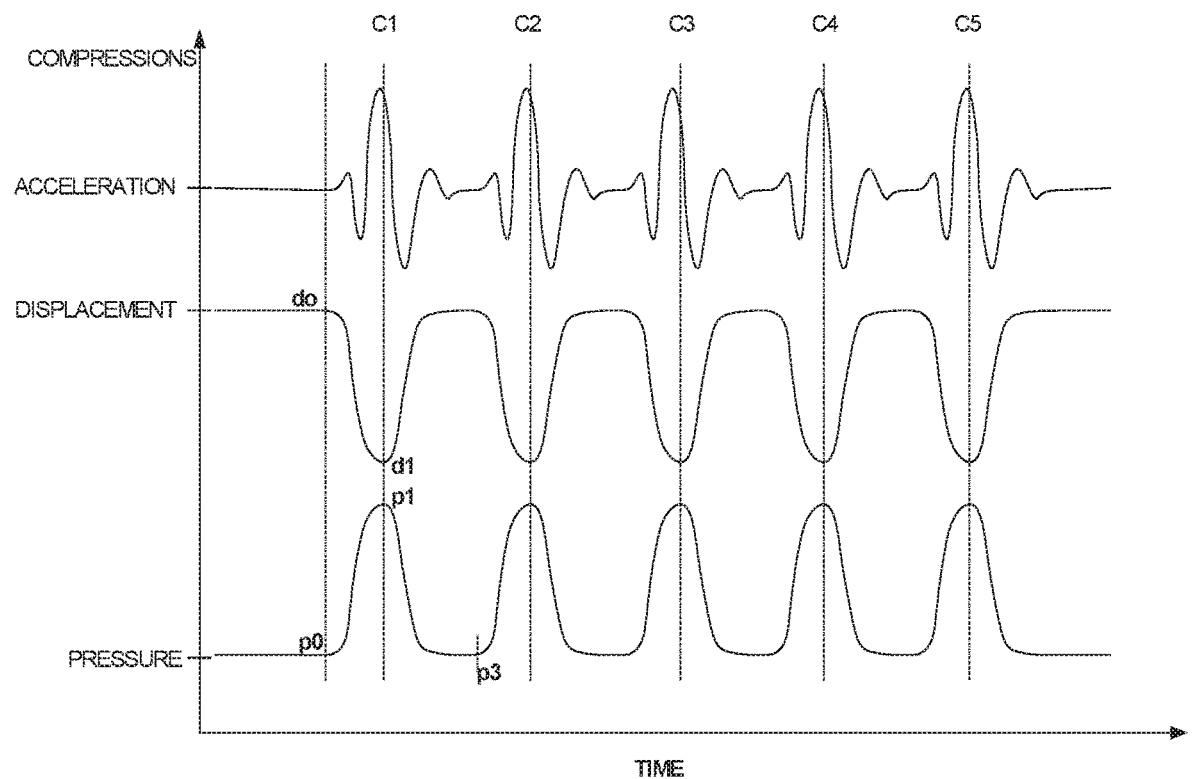
FIG. 2 shows sample signals recorded during CPR with the implementation of FIG. 1.

FIG. 2 shows a sample drawing of the signals recorded during CPR using the implementation of FIG. 1. The acceleration signal is band pass filtered and integrated to derive displacement information (e.g., a displacement signal). Compressions (C1-C5) can be detected from the displacement signal. The compression rate is calculated from the interval between compressions (e.g. (time of C2−time of C1)), and compression depth is measured from the compression onset to peak displacement (e.g. (d1−d0)). The onset and peak compression values are saved for each compression. The pressures at the compression onset and offset are used to determine the force used to achieve a given compression depth. The compliance of the chest can be estimated from the compression displacement and the related compression pressure. The pressure "p0" is the reference pressure prior to the start of CPR and is related to the resting chest displacement "d0". The pressure "p1" is the pressure required to achieve the displacement "d1". The chest compliance is estimated from the following equation:

$$\text{Chest Compliance} = |(d1-d0)/(p1-p0)|$$

Where d1 is the displacement at the peak of the compression, d0 is the displacement at the onset of the compression, p1 is the pressure at the peak of the compression, and p0 is the pressure at the onset of the compression. The chest compliance can be calculated for each compression and averaged to improve the measurement accuracy.

Once the patient specific chest compliance is known, it can be used to estimate the absolute displacement of the puck when combined with the instantaneous puck pressure measure from the following equation:

$$\text{Displacement} = \text{compliance} * (p-p0)$$

Where p is the pressure measured from the puck at a point in time, p0 is the resting puck pressure when there is no compressions or handling by the rescuer. Therefore, the chest release displacement can be estimated by the following equation:

$$\text{Displacement at the release of chest} = \text{compliance} * (p3-p0).$$

Where compliance is determined as described above, p3 is the chest release pressure (estimated as the onset pressure of the next compression), and p0 is the resting pressure.

The chest release pressure can alternately be measured as the minimum pressure point between the two compressions.

The chest release displacement point is compared to a pre-defined threshold level to determine if the chest was substantially released between two compressions (i.e., released sufficiently to create a pressure in the chest that facilitates venous filling of the heart). A combination of voice prompts and display messages can be used to tell the rescuer to more completely release the chest between compressions if the chest release displacement point does not return below the set threshold. The chest release displacement value can be averaged to improve the estimate accuracy. The comparison to the threshold level could also be done via "voting" logic such as the last x out of y values exceed the set threshold and trigger the release of chest feedback. The CPR release of chest algorithm continually runs while the rescuer performs CPR and provides immediate feedback if the rescuer does not release the chest at any time during the resuscitation.

Although not necessary, the threshold level is preferably adjusted dynamically as a function of the calculated chest compliance. For patients with a lower compliance, the threshold can be increased since increased force will have little or no effect on displacement. For patients with higher compliance, the threshold may need to be decreased.

The calculated estimate of chest compliance can also be used with the output of the force sensor to estimate the depth of chest compression. Thus, for example, the output of the accelerometer could be used with the output of the force sensor during an initial time interval to calculate an estimate of chest compliance. Thereafter, the estimated chest compliance could be used to convert the force measurement into an estimated depth of chest compression.

Figure 3:
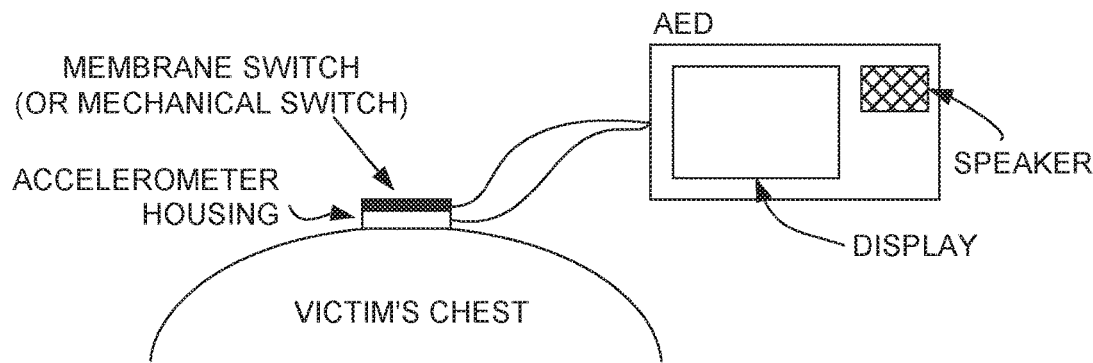
FIG. 3 is a diagram of another implementation including an AED with a membrane switch and an accelerometer.

FIG. 3 shows another implementation wherein the force sensor is replaced with a mechanical or electrical switch. The rescuer performs CPR by pressing on the switch/housing assembly. The switch is activated based on the forces used with CPR compressions and deactivated when a compression is released. The switch may provide for bistable positional states such as in a domed switch that when depressed would provide tactile feedback to the hand of the rescuer upon the start of the compression (dome collapse) and at the end of compression (dome return). The switch vibration associated with the transition between the two states may also be sufficient to provide an audible feedback to the rescuer as well. If the compression release vibration is heard and/or felt, the chest can be considered by the rescuer to have been released.

Figure 4:
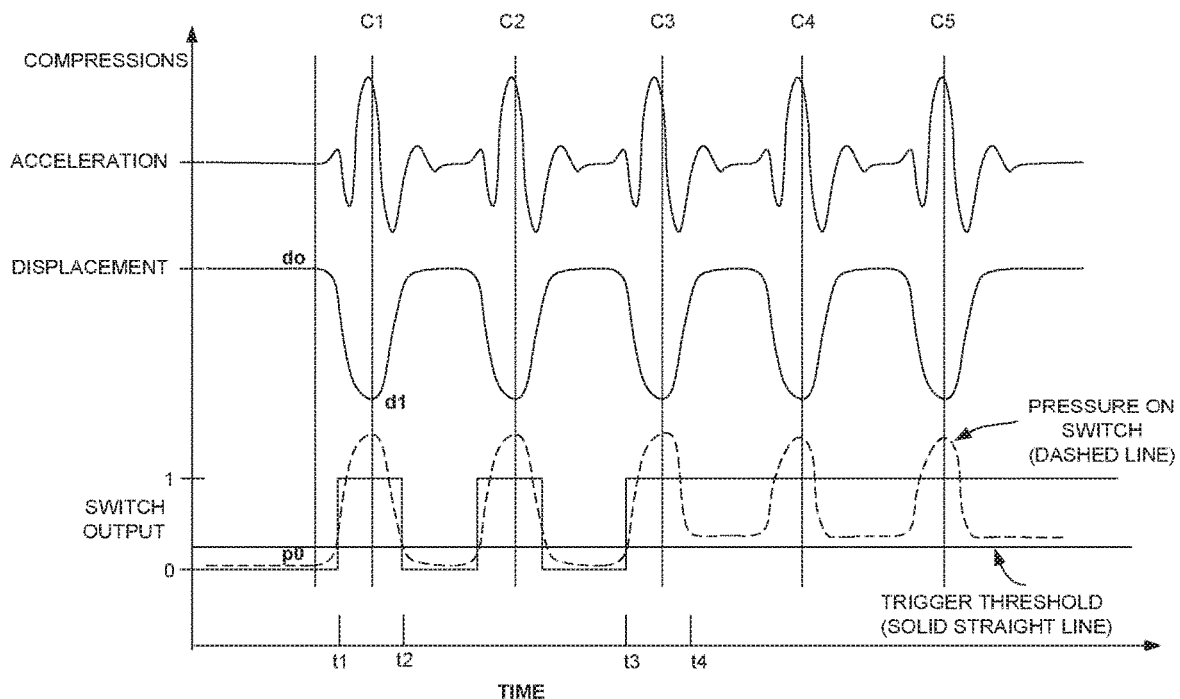
FIG. 4 shows sample signals recorded during CPR with the implementation of FIG. 3.

FIG. 4 shows the acceleration, derived displacement, and switch output signals during a sample of CPR. Each compression is identified at the top of the diagram (C1-C5). The compression interval, rate, and depth are measured from the acceleration signal. The dashed line overlaying the switch output curve indicated the force on the puck assembly and is drawn to show the actuation of the switch when the force curve exceeds that activation threshold (solid straight line). Time t1 shows the actuation of the switch and time t2 shows the release of the switch. On the third compression (C3), the compression switches (ON) at time t3, but does not switch off at time t4 because the force on the chest does not go below the trigger threshold. The acceleration signal shows that chest compressions are continuing, but the switch indicates that the chest is not being substantially released. When chest release is not occurring, the AED can audibly and/or visually prompt the user to release the chest.

Figure 5:
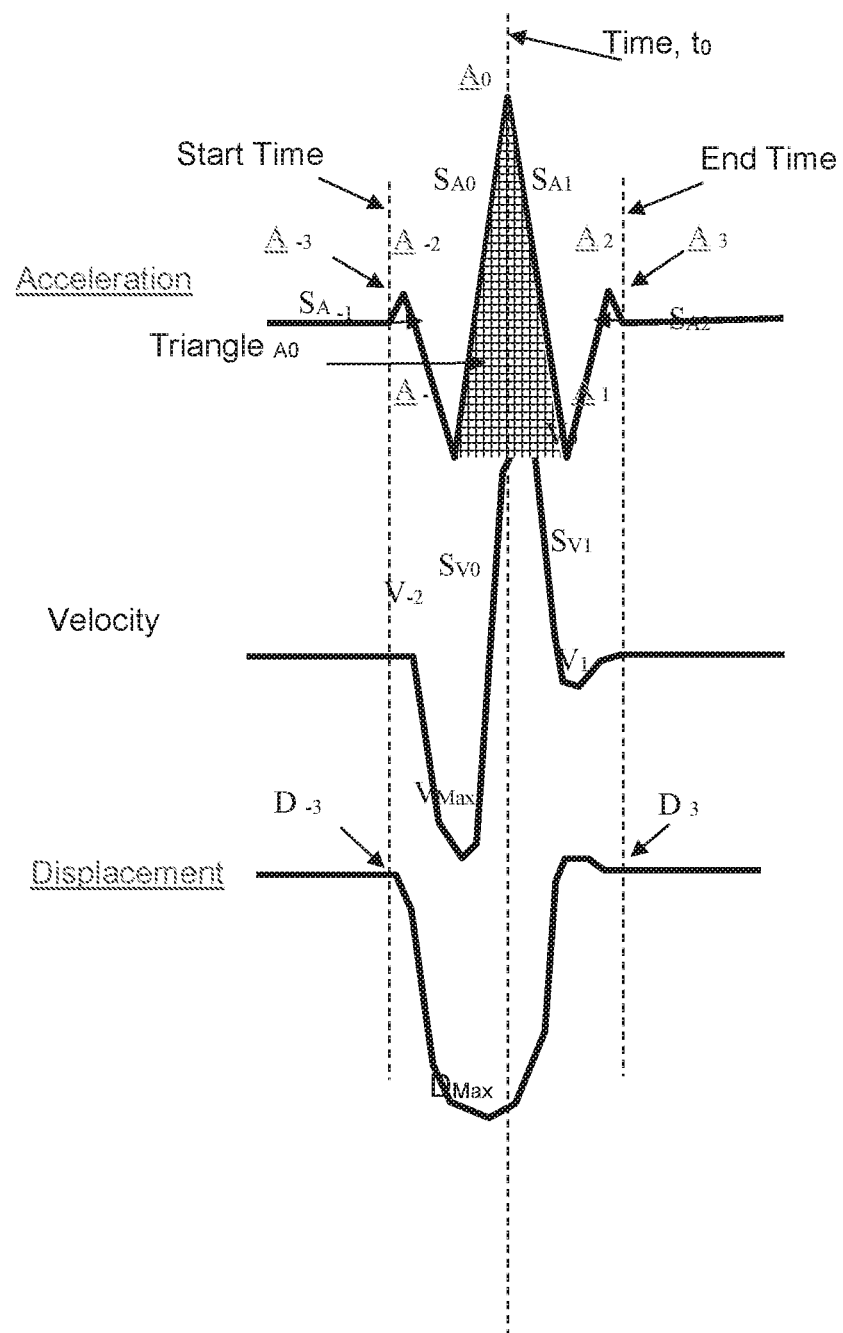
FIG. 5 depicts acceleration, velocity, and displacement for a single compression cycle.
Figure 6:
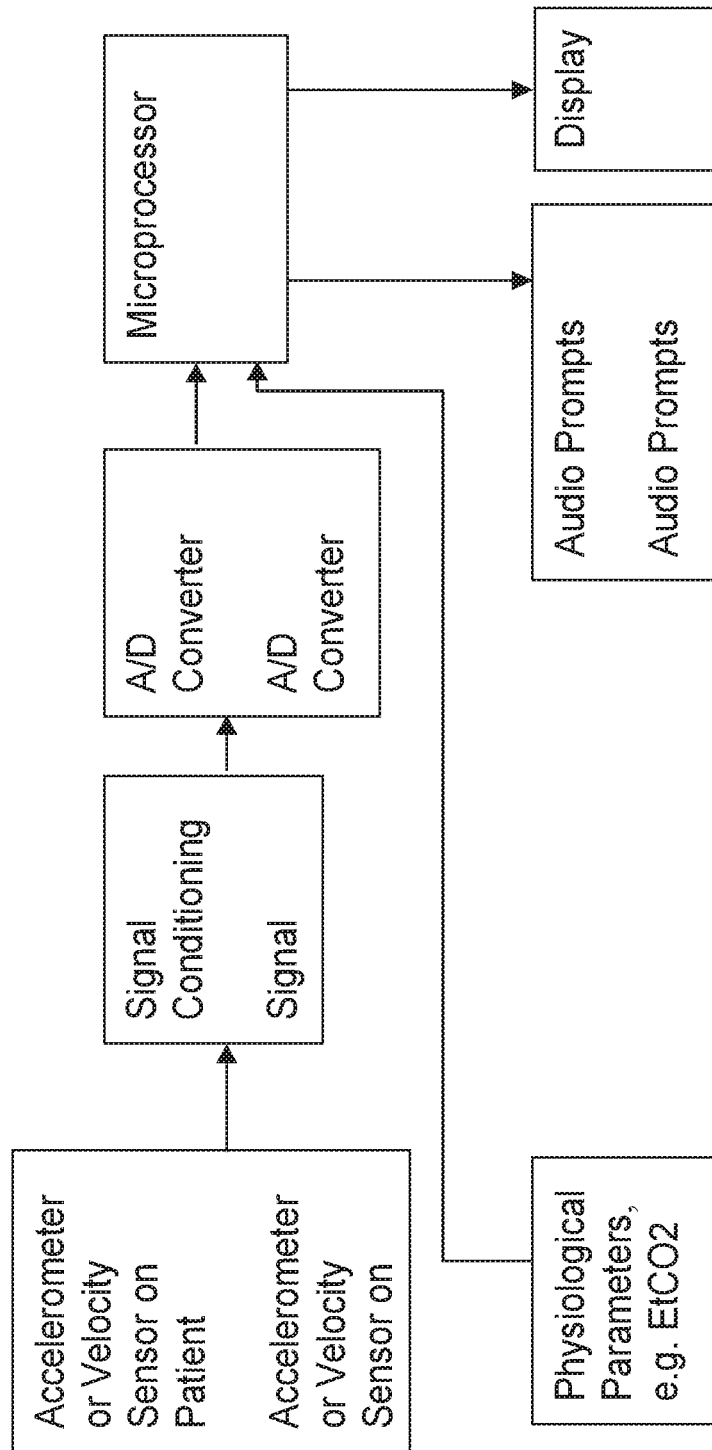
FIG. 6 is a block diagram of another implementation.

In another implementation, the acceleration waveform alone is analyzed without the use of a switch or force sensor. FIG. 5 depicts the acceleration, velocity and displacement for a single compression/decompression cycle. The input signal from the acceleration sensor, as shown in the block diagram in FIG. 6, is conditioned and filtered to minimized artifact and noise and is input to an A/D converter. The A/D converter is then read by the microprocessor. In FIG. 5, the points of interest in the acceleration waveform are as follows:

1. A0 is the point of maximum acceleration during the compression downstroke.
2. A−2 is the compensatory small upstroke that rescuers often do just prior to the initiation of the compression downstroke and marks the initiation point of the compression downstroke.
3. A−1 is the point of maximum acceleration of the compression downstroke.
4. A1 is the point of maximum deceleration on the decompression upstroke.

5. A2 is a small upward release when the rescuer's hands are slightly lifted from the patient's sternum during an optimum compression cycle.

6. A−3 and A3 are inflection points where the signal deviates from baseline.

7. SA0 and SA1 are the slopes of the acceleration of the line segments on each side of A0.

8. SV0 and SV1 are the slopes of the line segments (~acceleration) as shown on the velocity curve.

9. VMax is the maximum velocity achieved during the compression downstroke.

Many algorithms can be used for determination of substantial release of the chest. One algorithm is as follows:

1. Determine fiducial point A0. Completion of the compression determination should approach real time in order to provide maximum benefit to the rescuer. Delays of approximately 1-4 seconds are acceptable and will limit the types of 'search forward' algorithms that can be implemented. A0 can be detected by a number of means. One method is to band pass filter the acceleration signal to produce maximum output signal amplitude of signals having a slope most closely approximating those observed in real compression signals. The band pass output is then input to a threshold detection function. If the signal amplitude is larger than the threshold, then SA0 has been detected. The threshold itself may be dynamically adjusted in amplitude to minimize susceptibility to noise and interference. For instance, if out of band noise such as 60 Hz interference is detected, then the threshold may be increased. The threshold may also be gradually lowered following an SA0 detection such that the probability of detection is increased for signals that occur at the expected interval and is decreasing for false signals that may occur immediately subsequent to the detection. Once SA0 has been detected, the algorithm can search forward until it finds the peak amplitude, A0.

2. Searching backwards and forwards from point A0, the points A−3, A−2, A−1, A0, A1, A2 and A3 can be determined.

3. The acceleration signal can then be decomposed into constituent triangles formed from these fiducial points. TriangleA0 refers to the triangle formed by the A−1, A0 and A1 fiducial points (in gray in FIG. 5).

4. The triangles are then parameterized using such morphological characteristics as width, amplitude, area, center of mass, skewness, height/width ratio, etc.

5. Area ratios are then calculated for the various triangle pairs. For example the ratio of the areas of TriangleA0 and TriangleA1, Acceleration Triangular Area Ratio(0,1) [TARA(0,1)]

TARA(0,1)=[Area TriangleA0]/[Area of TriangleA1]

6. Amplitude ratios are then calculated for the various triangle pairs. Degree of skew is incorporated into the amplitude calculation by incorporating either skewness or center of mass into the calculation for each triangle. For example the ratio of the areas of TriangleA0 and TriangleA1, Triangular Amplitude ratioA(0,1) (TAMPRA(0,1))

TAMPRA(0,1)=[Amplitude of TriangleA0]/[Amplitude of TriangleA1]

7. The same process is repeated for the triangular width ratio (TWR).

Figure 7:
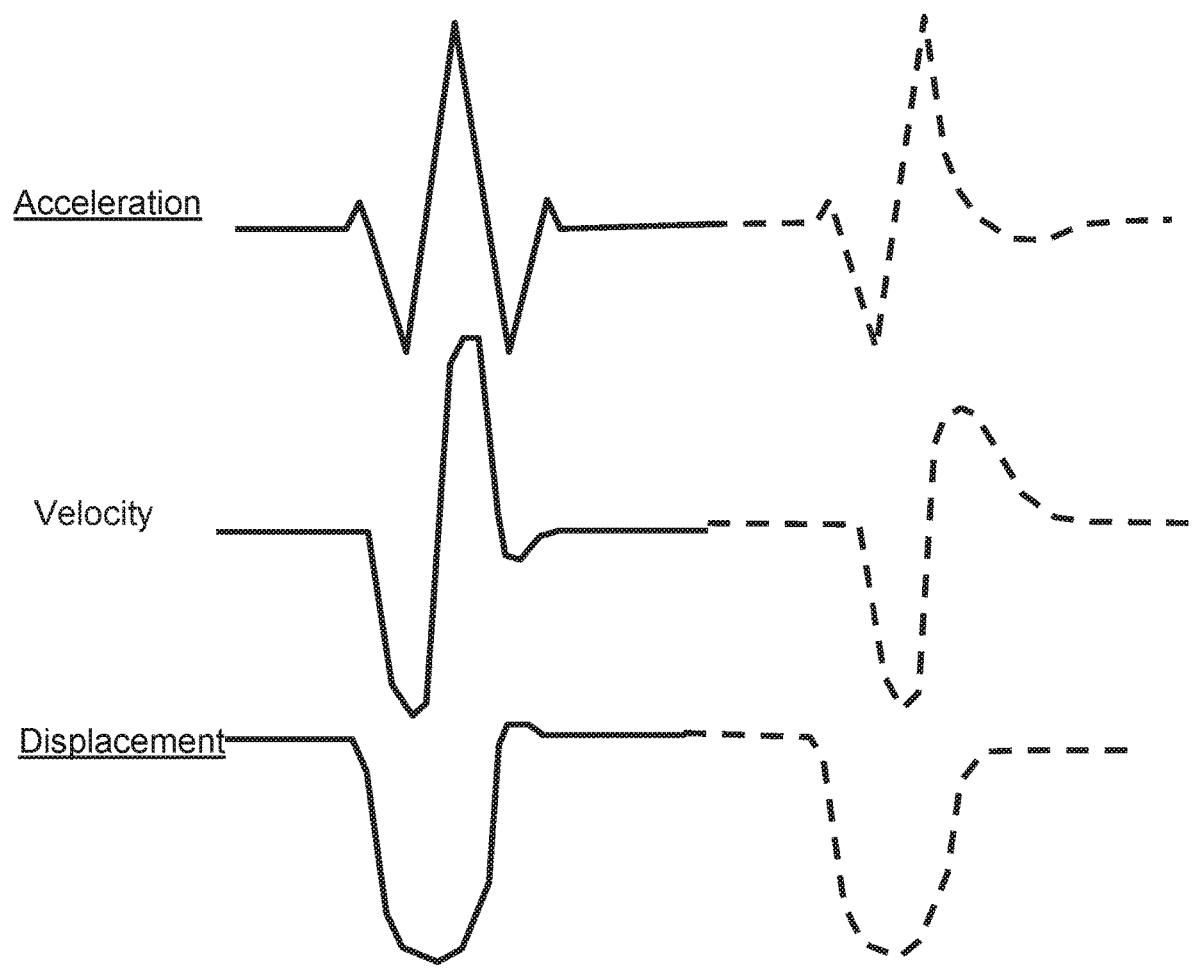
FIG. 7 depicts acceleration, velocity, and displacement for two compression cycles.

8. A rescuer who applies too much downward force during the decompression upstroke will cause incomplete decompression. This downward force opposes the natural elastic force of the thoracic cage and as a result causes a decreased amplitude and elongation of triangleA1 and triangleA2 as shown in FIG. 7.

9. The acceleration signal is integrated beginning at inflection point A−3 and ending just subsequent to A3 in order to calculate the velocity. The same analysis is used to calculate the fiducial points V−2, VMax, V0 and V1, as well as TAR, TAMPR and TWRs for the velocity curve.

10. The velocity curve segment is integrated a second time to calculate displacement. Displacement values D−3 and D3 and DMax are calculated. Differential displacement, ΔD=D−3−D3 is calculated.

11. Based on DMax, the device can prompt the rescuer if the depth of compressions are not sufficient.

12. Based on VMax, the user can be prompted to deliver a 'sharper' more rapid pulse to improve hemodynamics.

13. End tidal carbon dioxide (EtCO2) measurements are taken during the course of CPR. Visual and/or audible prompting from the device can encourage the rescuer to increase rate and depth of compressions to improve hemodynamics.

14. The calculated parameters of width, amplitude, area, center of mass, skewness, height/width ratio, TAR, TAMPR and TWR for both the acceleration and the velocity as well as ΔD are used to make a decision on whether the chest was released. The methods used may be standard decision logic (IF-THEN-ELSE) or may involve methods such as fuzzy-logic decision methodology or statistical estimation such as Bayesian methods. In general, ΔD alone would not be used to determine chest release, but nonetheless the signal processing methods have made it possible with this method to be able to measure ΔD without the use of switches or force sensors.

15. Final determination of compression release can be withheld for a number of compression cycles to measure longer term trending of the parameters. For example, the rescuer may have momentarily had to pause to wipe their brow.

Alternatively, other signal detection and classification methods known to those skilled in the art may be used to determine the relevant morphological features such as those shown in FIG. 7 (CPR with substantial chest release is shown by solid lines; inadequate chest release, by dashed line).

Figure 8:
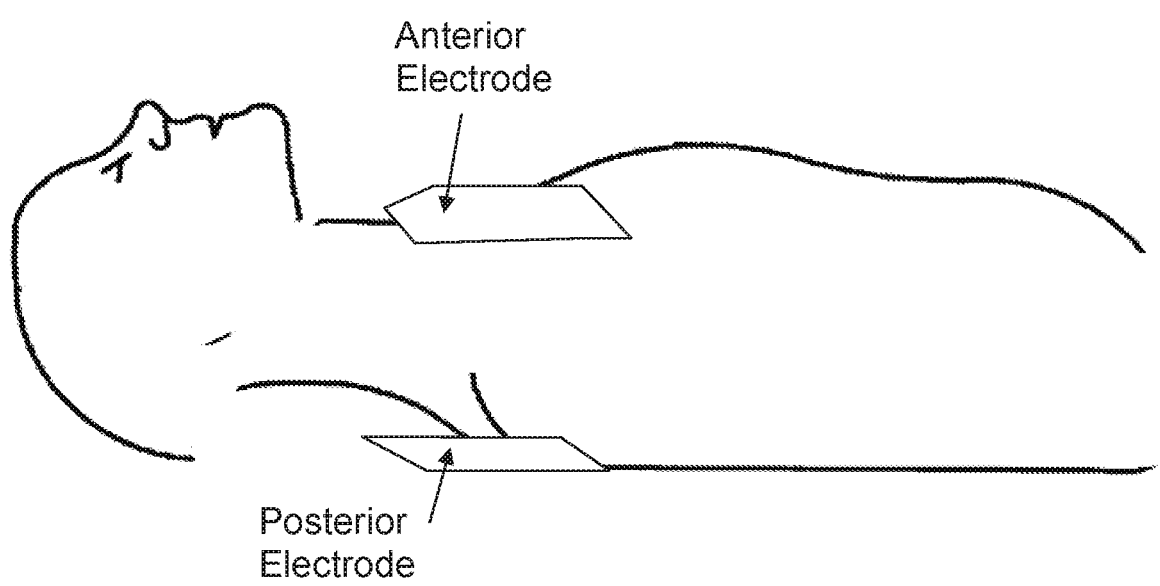
FIGS. 8, 9A, and 9B show an implementation in which magnetic induction elements are built into electrodes placed in anterior and posterior locations on the thorax.
Figures 9A, 9B:
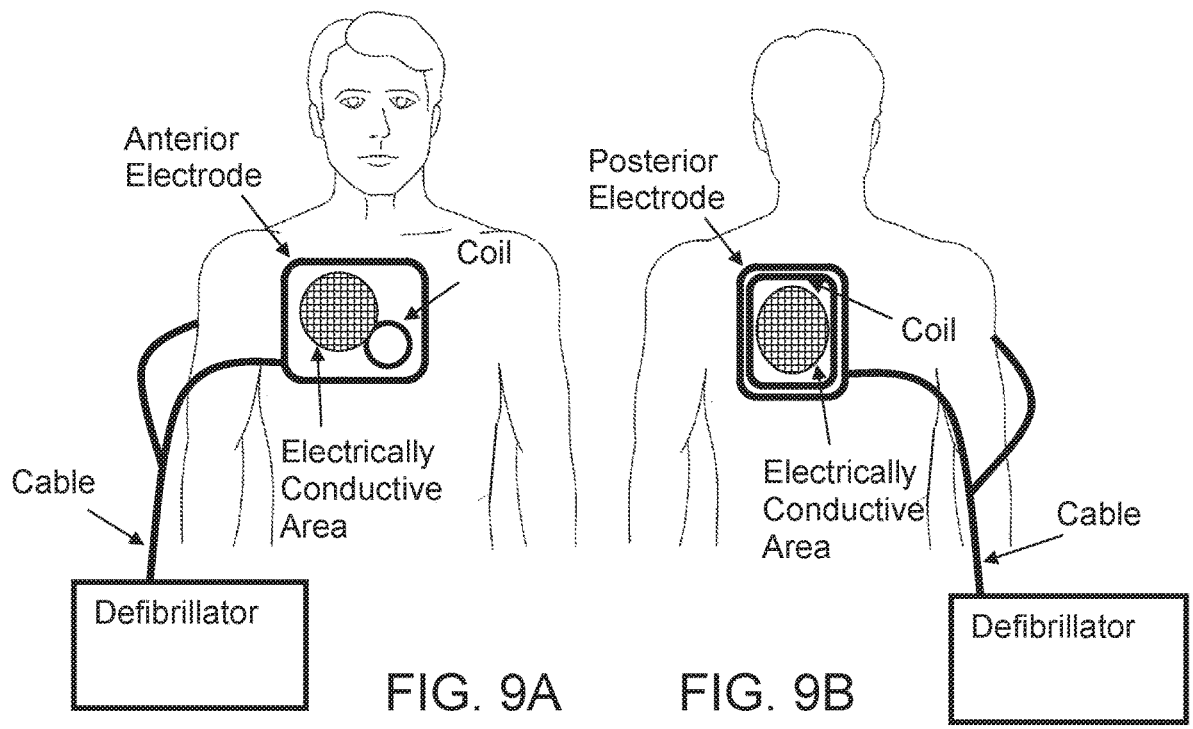

In another implementation, a velocity sensor is used to determine the motion parameters. One of many possible techniques for sensing velocity is to use magnetic induction to generate a voltage proportional to the relative velocity between a magnet and coil. The configuration is shown in FIG. 8. The magnet may take the form of a permanent magnet, but preferably it is an electromagnet. As shown in FIGS. 9A and 9B, a defibrillation pad is placed on the left thorax and another defibrillation pad is placed on the victim's back in the left scapular area. These are optimal locations for defibrillation and provide a good placement to generate magnetic flux changes proportional to sternal displacement. The coils are incorporated directly into the outer edge of each of the defibrillation electrodes. Alternatively, if the desired electrode position is anterior/anterior with both electrodes on the front of the chest, a separate backboard panel may be supplied which is placed under the patient and contains the receiving coil. The use of an electromagnet serves two main purposes: it can be used to calibrate the setup after the electrodes have been applied to the patient and they can be used to provide a synchronous modulation/demodulation of the signal to improve accuracy and minimize susceptibility to noise and artifact.

Figure 10:
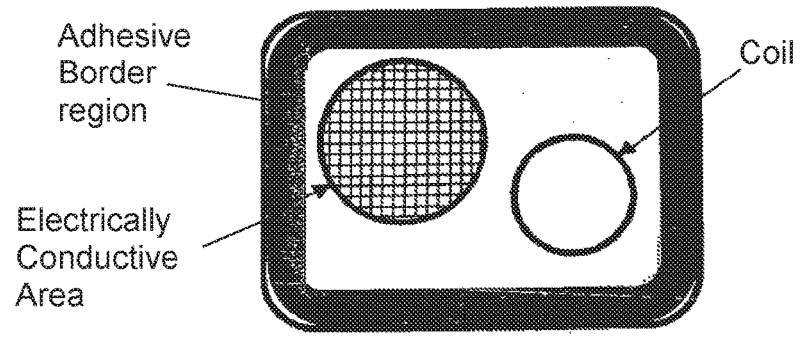
FIG. 10 is an enlarged view of the composition of the electrode pad of FIG. 9A.

The defibrillation electrodes can be constructed with a conventional configuration. An electrically conductive sheet of material that delivers defibrillation current to the patient is backed with an insulating thin foam material, and a slightly adhesive conductive gel coupling agent adheres the conductive sheet to the patient's skin. The foam backing also forms an approximately 0.5 to 1.0 inch border around the active conductive area. The magnetic coil element can be added onto the foam backing and becomes part of the border area, as shown in FIG. 10.

The device (e.g., AED) can be provided with circuitry for determining whether or not the electrodes have been properly applied to the patient. The method currently employed by most manufacturers of defibrillators is to use a small amplitude, high frequency signal (~2 microamps, 60 KHz) to measure impedance. The electrodes are determined to be applied when the impedance falls into the physiologic range.

When the device has detected the application of the electrodes, the device can prompt the rescuer to stand clear. At this time, the device will perform calibration of the velocity sensor. A time-varying signal, typically a ramp or sine wave of several frequencies of interest, such as the modulation frequency, is applied to the electromagnet and the signal is measured at the receiving coil. From this, gain and offset coefficients can be calculated for use during the CPR event. This calibration step allows for improved accuracy with patients of varying chest sizes and in the presence of any nearby magnetically conductive surfaces or objects.

Figure 11:
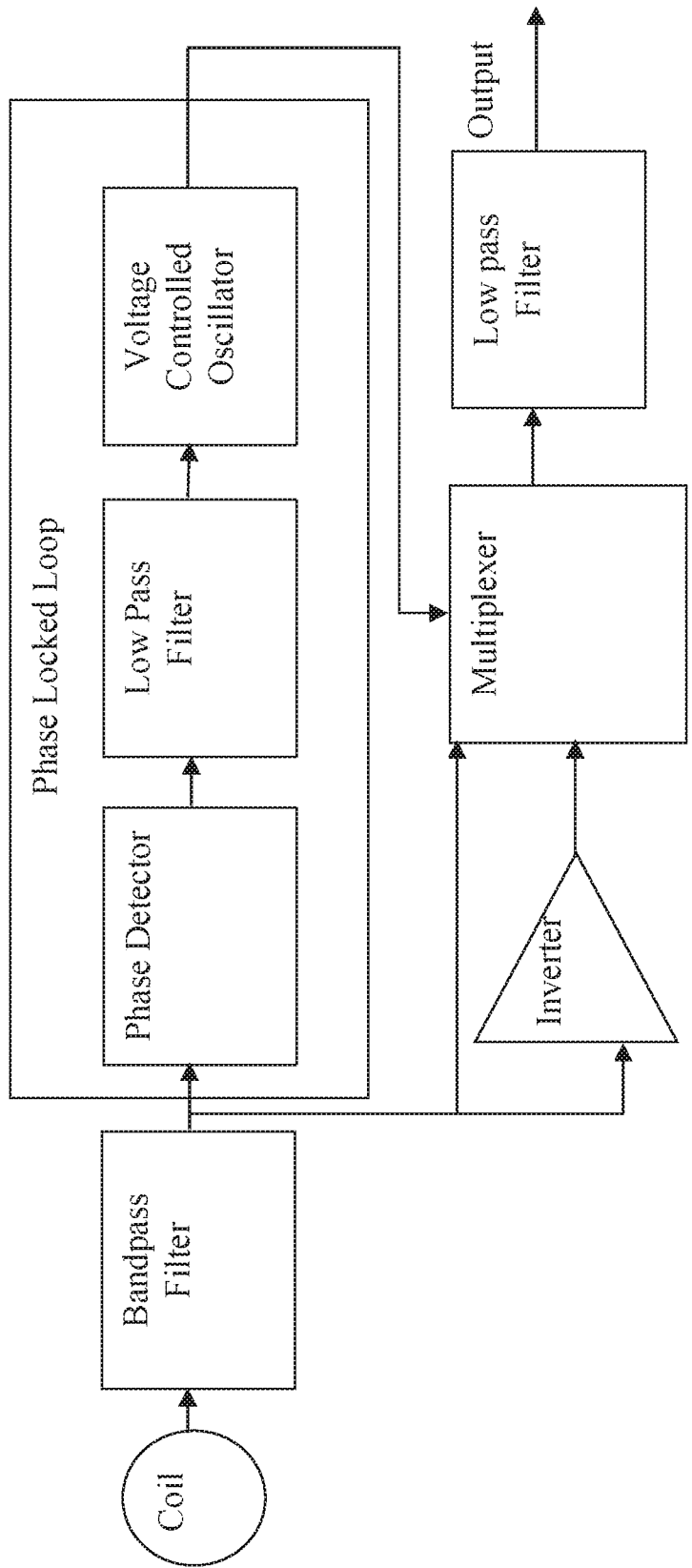
FIG. 11 is a block diagram of a synchronous detector implementation.

Preferably, a synchronous detector can be employed to minimize susceptibility to noise and artifact as shown in the block diagram in FIG. 11. A sine wave carrier frequency of 500 Hz or more is supplied to the electromagnet coil to generate an oscillating magnetic field that, in turn, induces a voltage on the receiving coil. Chest compressions vary the field intensity at the receiving coil, thus causing an amplitude modulation of the carrier. As can be seen in FIG. 11, a band pass filter immediately subsequent to signal reception reduces interference outside the range of the carrier frequency such as AC magnetic interference. The phase lock loop (PLL) is used for carrier regeneration, but since the transmitter and receiver are in the same device, the transmission carrier can be used for detection as well, as long as circuitry is provided for phase adjustment of the demodulation signal. Multiplexer Si, combined with the demodulation signal, causes rectification of the signal, which can then be low pass filtered to recover the compression velocity waveform. Alternatively, a synchronous AM demodulator can be employed with an analog multiplier stage.

In another implementation, the velocity signal may then be used to reduce artifacts in the ECG signal. This is accomplished by first time-aligning the ECG and velocity signal by such methods as cross-correlation techniques known to those skilled in the art. This will provide alignment of the two signals relative to the compressions. Then, preferably, adaptive filtering methods are used such as those involved in the minimization of the mean-squared error between the ECG and the velocity.

Figure 12:
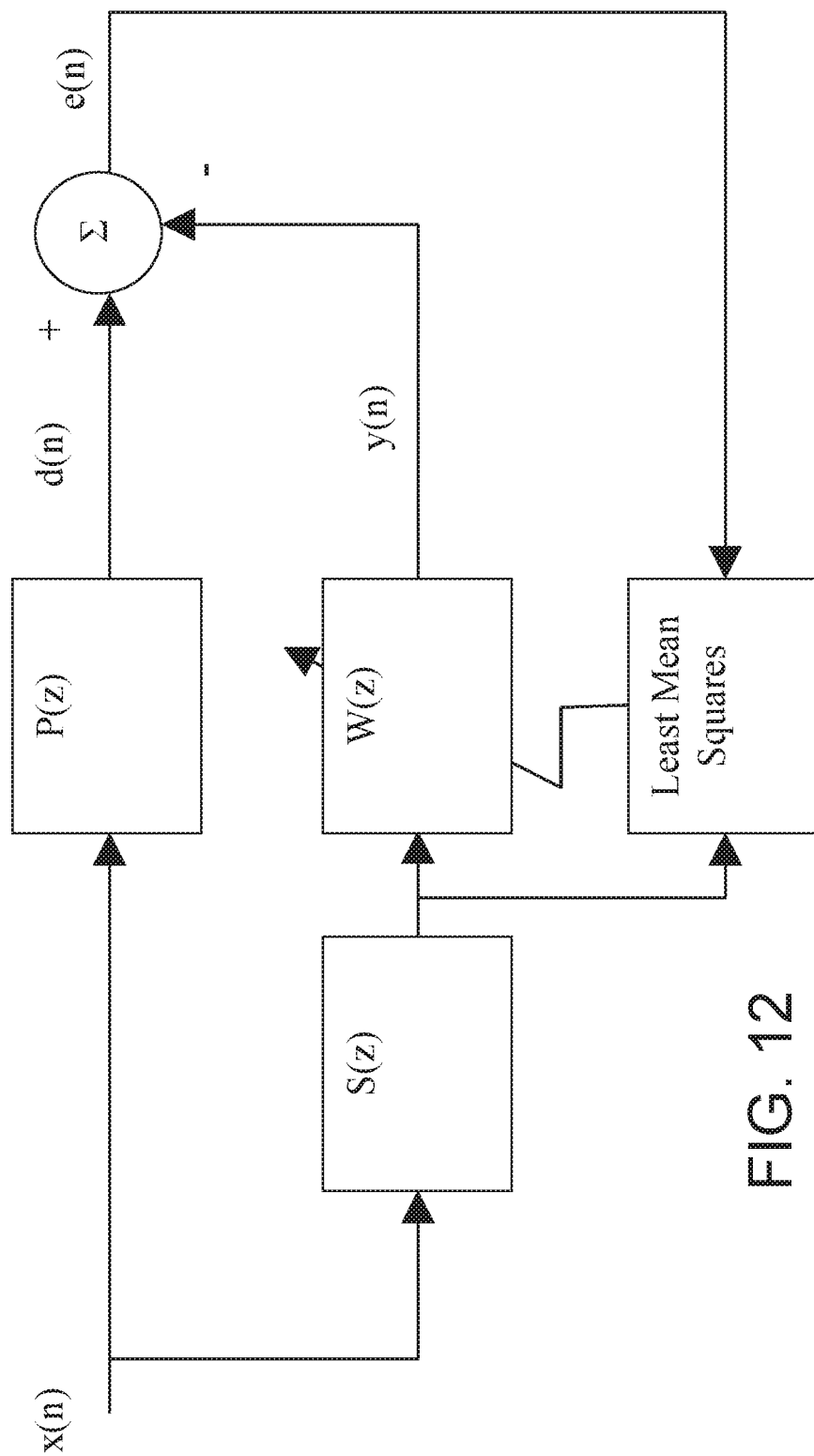
FIG. 12 is a block diagram of a filtered-X least mean squares (FXLMS ANC) algorithm.
Figure 13:
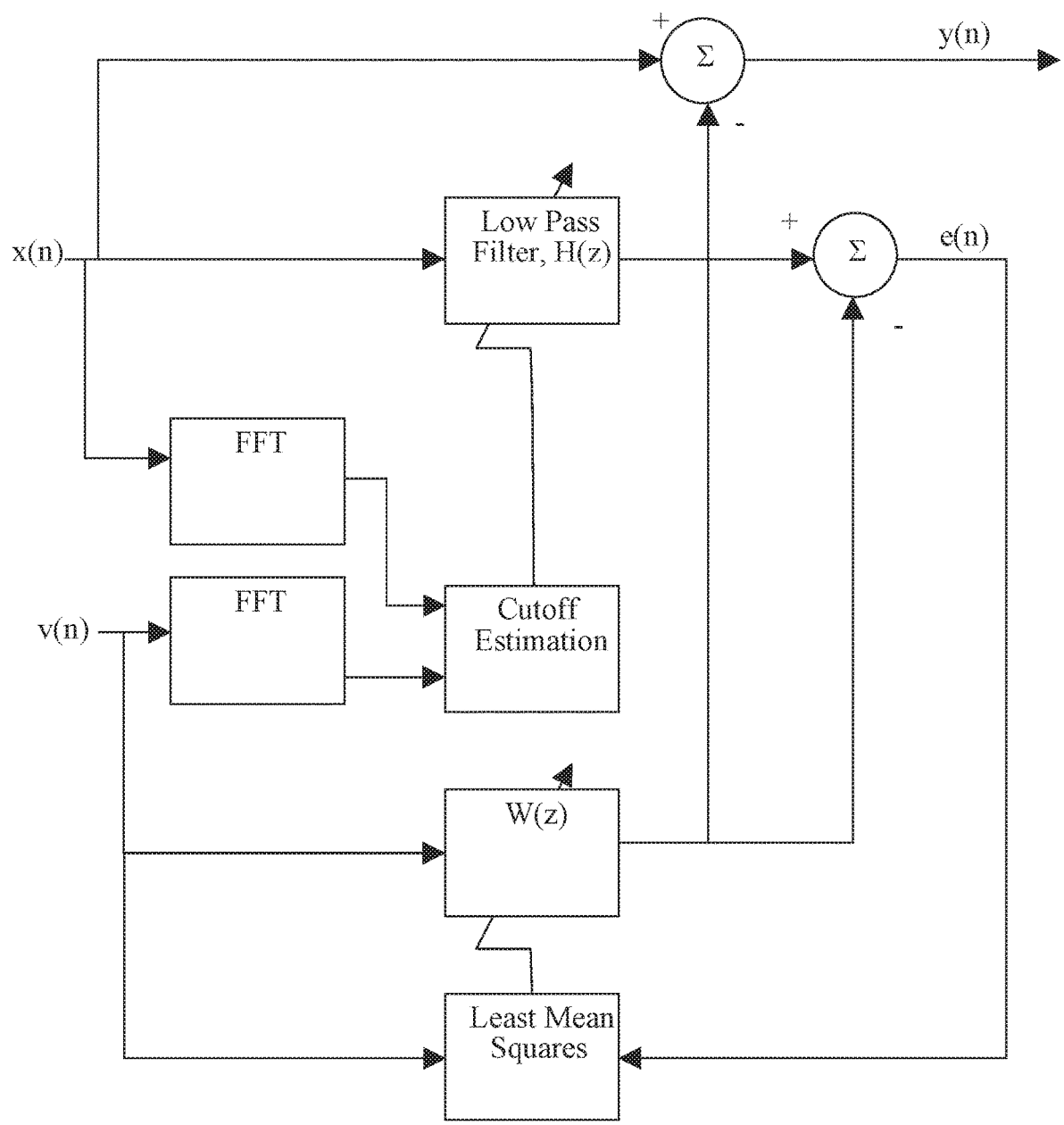
FIG. 13 is an implementation using the algorithm of FIG. 12.
Figure 14:
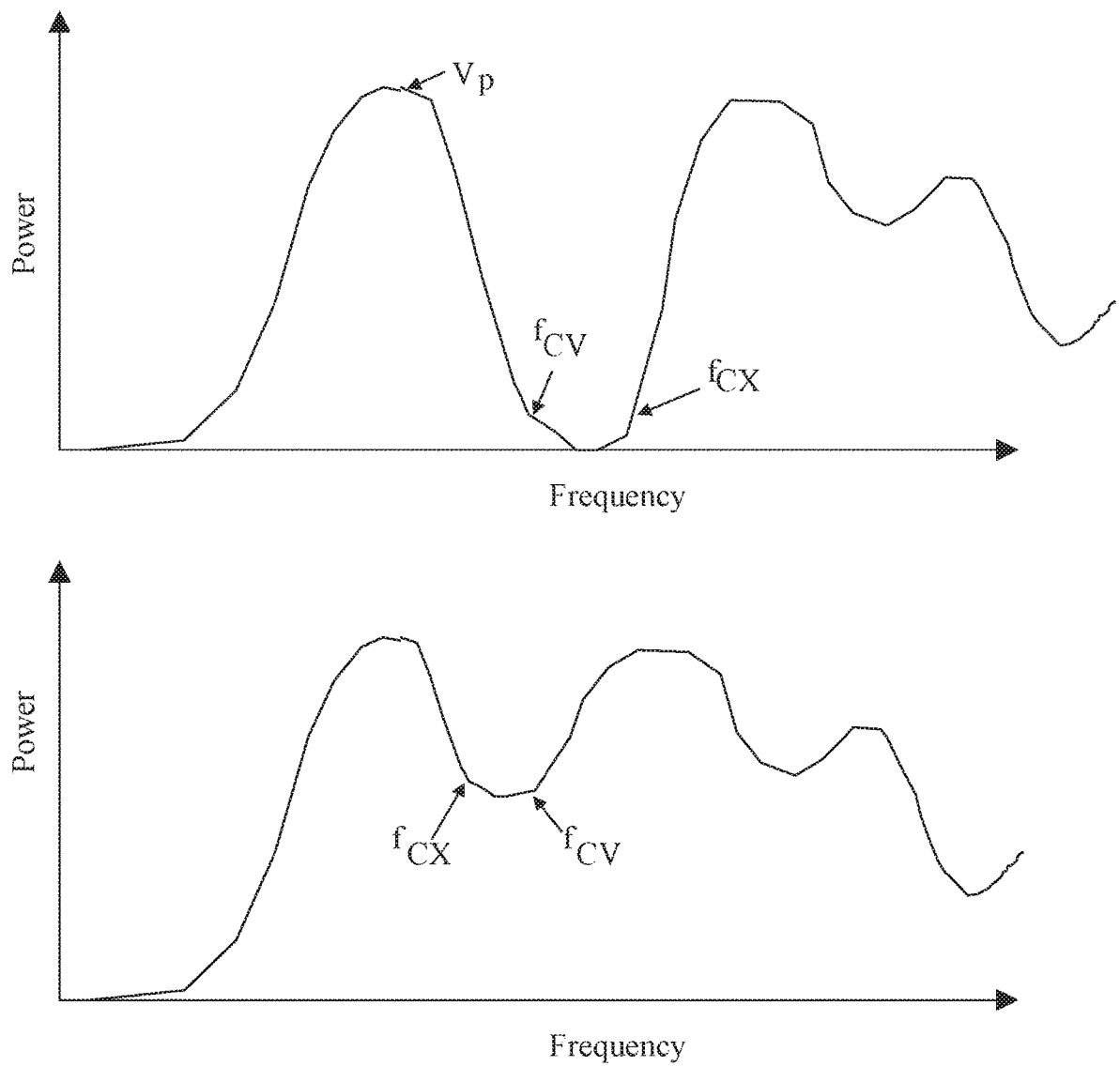
FIG. 14 shows two spectral power distributions related to the implementation of FIG. 13.

In a further implementation, more sophisticated signal processing methods may be used to minimize ECG artifacts induced by CPR chest compressions. For example, methods known as feed forward active noise cancellation (FANC) may be used. FIG. 12 shows a block diagram of the filtered-X least mean squares (FXLMS ANC) algorithm, as developed by Widrow and Burgess. P(z) represents the unknown plant through which the signal x(n) is filtered. Digital filter W(z) is adaptively adjusted to minimize the error signal e(n). In one implementation, as depicted in FIG. 13, x(n) is the unfiltered ECG signal, P(z) is eliminated from the diagram, and d(n) is approximated with the chest compression velocity signal v(n). In the LMS algorithm, assuming a mean square cost function $\xi(n)=E[e2(n)]$, the adaptive filter minimizes the instantaneous squared error, $\xi(n)=e2(n)$, using the steepest descent algorithm, which updates the coefficient vector in the negative gradient direction with step size μ:

$$w(n+1)=w(n)-\mu/2*\tilde{N}\xi(n),$$

where $\tilde{N}\xi(n)$ is an instantaneous estimate of the mean square error (MSE) gradient at time n equal to $-2v(n) e(n)$. Stability and accuracy of the FXLMS ANC algorithm by adding a variable cutoff low pass filter H(z) to eliminate frequency components in the ECG not related to the chest compression artifact. In general, the spectral energy of the chest compression artifact is predominately lower than those of the ECG. A cutoff frequency of approximately 3 Hz is adequate in many cases, but this may vary from patient to patient and among different rescuers performing chest compressions. To overcome this difficulty, an FFT is performed on v(n) and input into a cutoff frequency estimation (CFE) procedure that determines the optimal cutoff frequency, fC, for the lowpass filter. In a preferred implementation, the decision is based on calculating the frequency, not to exceed 5 Hz, below which 80% of the waveform energy is present, but this percentage may vary and additional decision logic may be employed. For instance, an FFT may also be calculated for x(n), also input to the CFE procedure. By first normalizing amplitude of the frequency spectra X(z) amplitude peak of the compression artifact and then subtracting the velocity spectra V(z) from the normalized input X'(z), the difference spectra is calculated $\Delta X'(z)=X'(z)-V'(z)$. Frequencies are then determined for V(z) and $\Delta X'(z)$ at which most of the spectral energy is within, set in this embodiment to 97%, and labeled fCV and fCX, respectively, and shown in FIG. 14. FC is then set to the lesser of fCV and fCX. Alternatively, fC can be set to some intermediate frequency between fCV and fCX.

Figure 15:
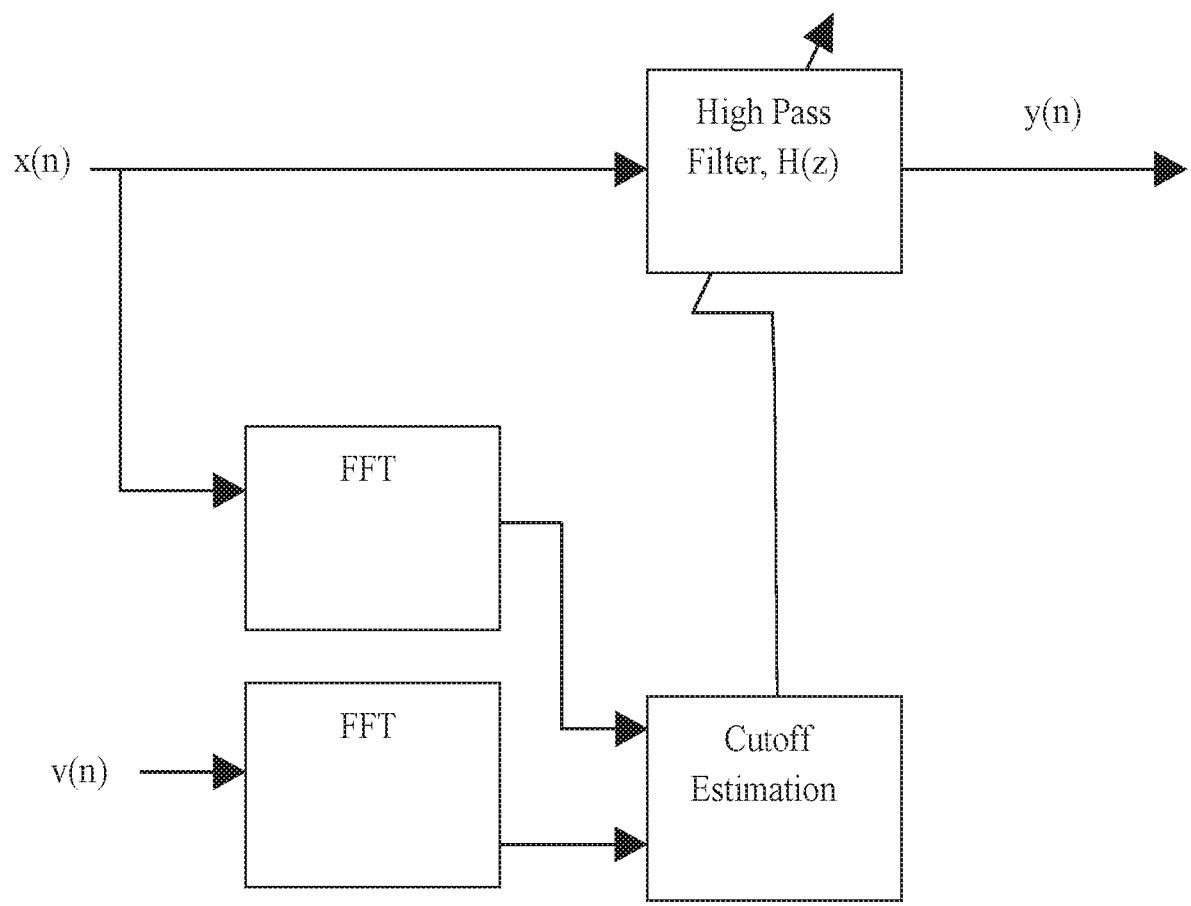
FIG. 15 is a block diagram of another implementation.

A simpler though related implementation is shown in FIG. 15, in which the CFE procedure is used to calculate the cutoff frequency for a high pass filter. Using the same methods as described in the previous paragraph, an FFT is performed on v(n) and input into a cutoff frequency estimation (CFE) procedure that determines the optimal cutoff frequency, fC, for, in this case, a high pass filter. In the preferred embodiment, the decision is based on calculating the frequency, not to exceed 5 Hz, below which 80% of the waveform energy is present, but this percentage may vary and additional decision logic may be employed. An FFT may also be calculated for x(n), and also input to the CFE procedure and the optimal high pass cutoff frequency can be determined by the methods described in the previous paragraph. For instances when the spectral energy of the compression artifact is distinct from the ECG signal, this method will have a performance equivalent to the FXLMS just described; its performance will be somewhat inferior when the spectra of the ECG and compression artifact overlap, however.

Figure 16:
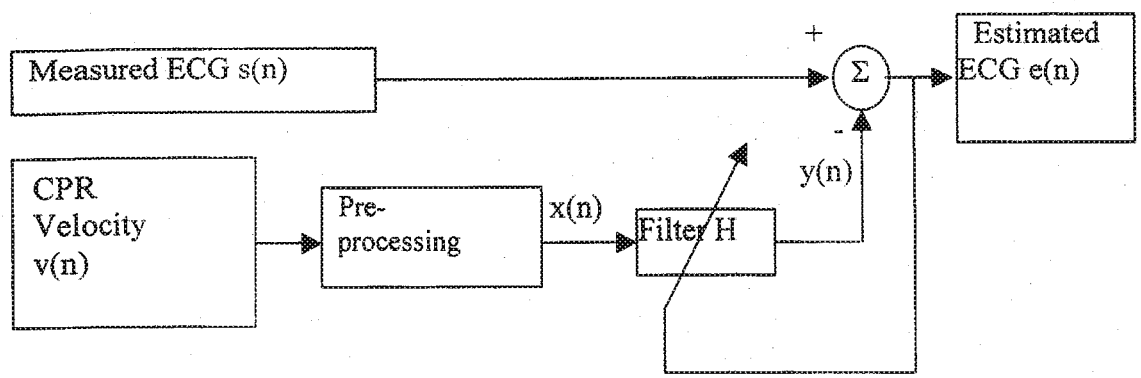
FIG. 16 is a block diagram of one implementation of the invention.

One possible implementation is illustrated by a flow chart in FIG. 16. The front end of an AED acquires both the ECG signal and the CPR signal, which is the velocity of compression of the chest. If chest displacement or acceleration are measured instead of velocity, velocity can be mathematically acquired via one or more integration or differentiation operations from the measurement signal.

The velocity signal undergoes pre-processing, and is then fed to an adaptive filter. In a preferred implementation, the pre-processing is a normalization of the velocity signal so that the signal supplied to the adaptive filter is limited to be within 0 and 1. But normalization is not required. In another implementation, a time-aligning process is performed on the ECG and the reference signal by such methods as cross-correlation. This provide alignment of the two signals relative to the compressions so that the input signals of the adaptive filter are better aligned. But this aligning process is not required. Other preprocessing can be applied to the velocity signal to improve the performance of the adaptive filter.

In FIG. 16, x(n) and y(n) are the input and the output of the adaptive filter H, which can be an FIR filter, an IIR filter, or another type of filter. In a preferred implementation, the coefficients of the filter are dynamically controlled by the estimated ECG signal:

$$h(n)=h(n-1)+m \times e(n) \times X(n)$$

where h(n) is a vector containing the filter coefficients, m is a vector containing the step sizes for each filter coefficients, e(n) is the estimated ECG signal, and X(n) is a vector containing the input data. The estimated ECG signal is computed by subtracting the filter output y(n) from the measured ECG signal (containing artifact).

In some implementations, there is an automated resetting mechanism. When the difference between the filter output y(n) and the measured ECG s(n) is beyond a threshold, the adaptive filter will reset its coefficients so that the system will not become unstable.

Other filter structures than the one shown in FIG. 16, as well as other mathematical representations of the filtering, are possible.

Figure 17:
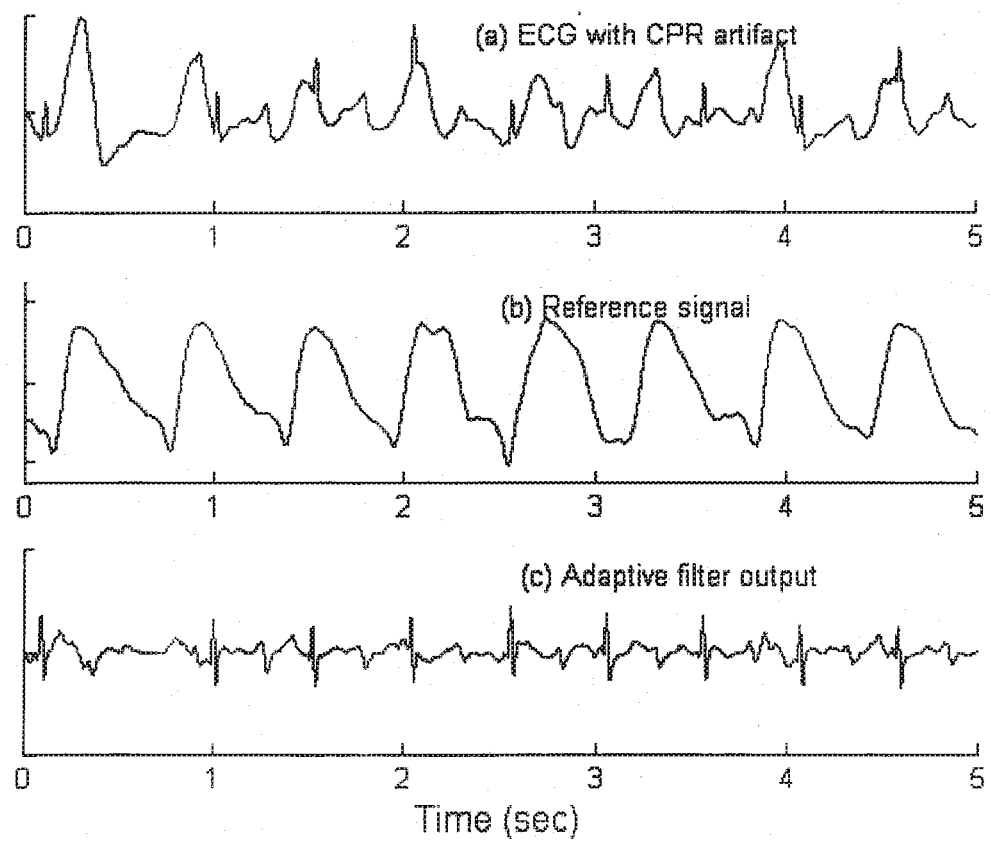
FIG. 17 shows plots of the ECG signal, CPR reference signal, and output of adaptive filter for a normal sinus rhythm.

FIG. 17 shows samples of the performance of the adaptive filter of FIG. 16 in response to a normal sinus rhythm. The signal in (a) is the ECG signal with CPR artifact. The signal in (b) is the compression velocity used as the reference signal. The signal in (c) is the output of the adaptive filter.

Figure 18:
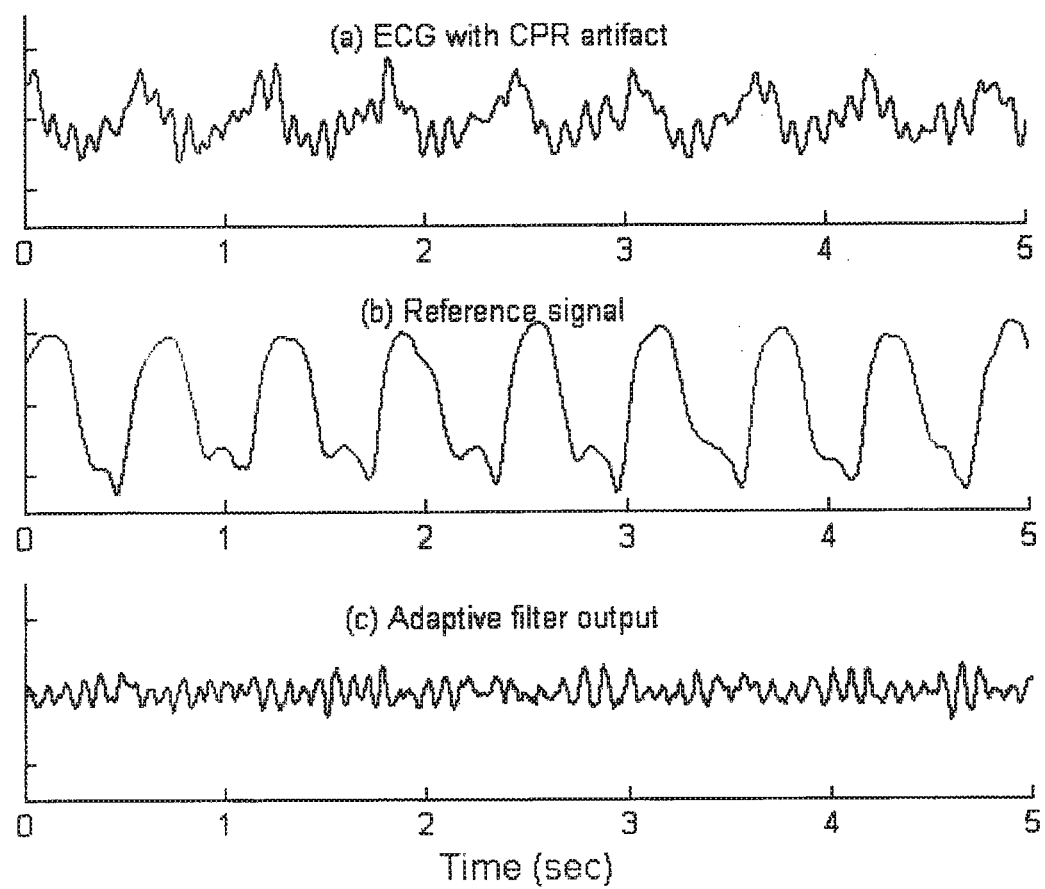
FIG. 18 shows plots of the ECG signal, CPR reference signal, and output of adaptive filter for ventricular fibrillation.

FIG. 18 shows samples of the performance of the adaptive filter of FIG. 16 during ventricular fibrillation. The signal in (a) is the ECG signal with CPR artifact. The signal in (b) is the compression velocity used as the reference signal. The signal in (c) is the output of the adaptive filter.

As shown in both FIG. 17 and FIG. 18, the implementation of FIG. 16 is able to suppress the CPR artifacts embedded in the measured ECG signals (a). The CPR artifact is nearly, if not completely, removed in the estimated ECG signal (c). The velocity signal (b) used as a reference signal is clearly correlated with the CPR artifacts in the measured ECG signals (a).

The adaptive filter assumes that the artifact in the signal is correlated with the reference signal and uncorrelated with the desired signal (estimated ECG). It thus adaptively estimates the artifact using the reference signal and subtracts the estimated artifact from the measured ECG signal.

The results shown in FIG. 17 are based on a 0th-order FIR filter, which simply scales the current sample of the ECG signal adaptively. The CPR artifact was significantly reduced, if not completely removed. This implementation thus combines simplicity and efficiency in its performance.

In the applications of adaptive filters, the speed of adaptation convergence is usually controlled by a step-size variable. A faster convergence requires a larger step size, which usually tends to make the filter less stable. The automatic resetting mechanism of some implementations can dynamically change the step size and thus improve the relation of convergence and stability.

The coefficients of the filter are updated in a sample-by-sample manner. The changes of the coefficients, i.e., h(n)−h(n−1) is proportional to the product of the step size and the reference signal. The amplitude of the reference signal can thus affect the stability and convergence of the filter. The pre-processing of the reference signal can therefore enhance the performance of the filter by adjusting the reference signal.

In another implementation, a time-aligning process is performed on the ECG and velocity signals by such methods as cross-correlation. This provide alignment of the two signals relative to the compressions. Then, preferably, adaptive filtering methods are used such as those involved in the minimization of the mean-squared error between the ECG and the velocity.

A processing unit could be provided for detecting when compressions are being applied and automatically turning on the adaptive filter. The output of the adaptive filter (i.e., the ECG signal with artifact reduced) could be supplied to a ventricular fibrillation (VF) detection algorithm (e.g., a shock advisory algorithm) of an automatic external defibrillator (AED).

An error signal could be produced that is representative of the difference between the ECG input and ECG output of the adaptive filter. This error signal would give a measure of the amount of CPR artifact in the signal, and it would be useful as a means of modifying the subsequent processing of the ECG. For instance, if the artifact level gets high enough (e.g., higher than a first threshold), the VF detection algorithm thresholds could be increased to make it more resistant to any CPR artifact that still remained in the ECG signal. If the level got even higher (e.g., higher than a second threshold higher than the first threshold), the VF detection could be shut off entirely.

In preferred implementation, the filter output is presented graphically on the display of a defibrillator or other medical device incorporating an electro-cardiographic function. The filter output may also be printed on a strip-chart recorder in the medical device. Alternatively, the filter output may provide the input signal for subsequent signal processing performed by the processing means. The purpose of such signal processing may take the form of QRS detection, paced beat detection during pacing, arrhythmia analysis, and detection of ventricular fibrillation or other shockable rhythms.

Spectral analysis could be performed on the error signal, and based on the major bands of frequency content of the error signal, the pre-filtering of the ECG signal prior to the VF detection can be adjusted. For instance, if the error signal is found to reside primarily in the 3-5 Hz band, additional filtering can be provided in that band prior to input into the VF detection (or other ECG processing) algorithm.

Many other implementations of the invention other than those described above are within the invention, which is defined by the following claims.

For example, methods of adaptive channel equalization may be employed to ameliorate both synchronization and phase errors in the velocity waveform. Kalman filtering techniques may also be employed to improve performance of the filter when rescuer performance of chest compressions changes over time and is better modeled as a non-stationary process.

Time alignment of the ECG and velocity signal may also be accomplished by such methods as cross-correlation techniques known to those skilled in the art. This will provide alignment of the two signals relative to the compressions. Then, preferably, adaptive filtering methods are used such as those involved in the minimization of the mean-squared error between the ECG and the velocity.

Figure 19:
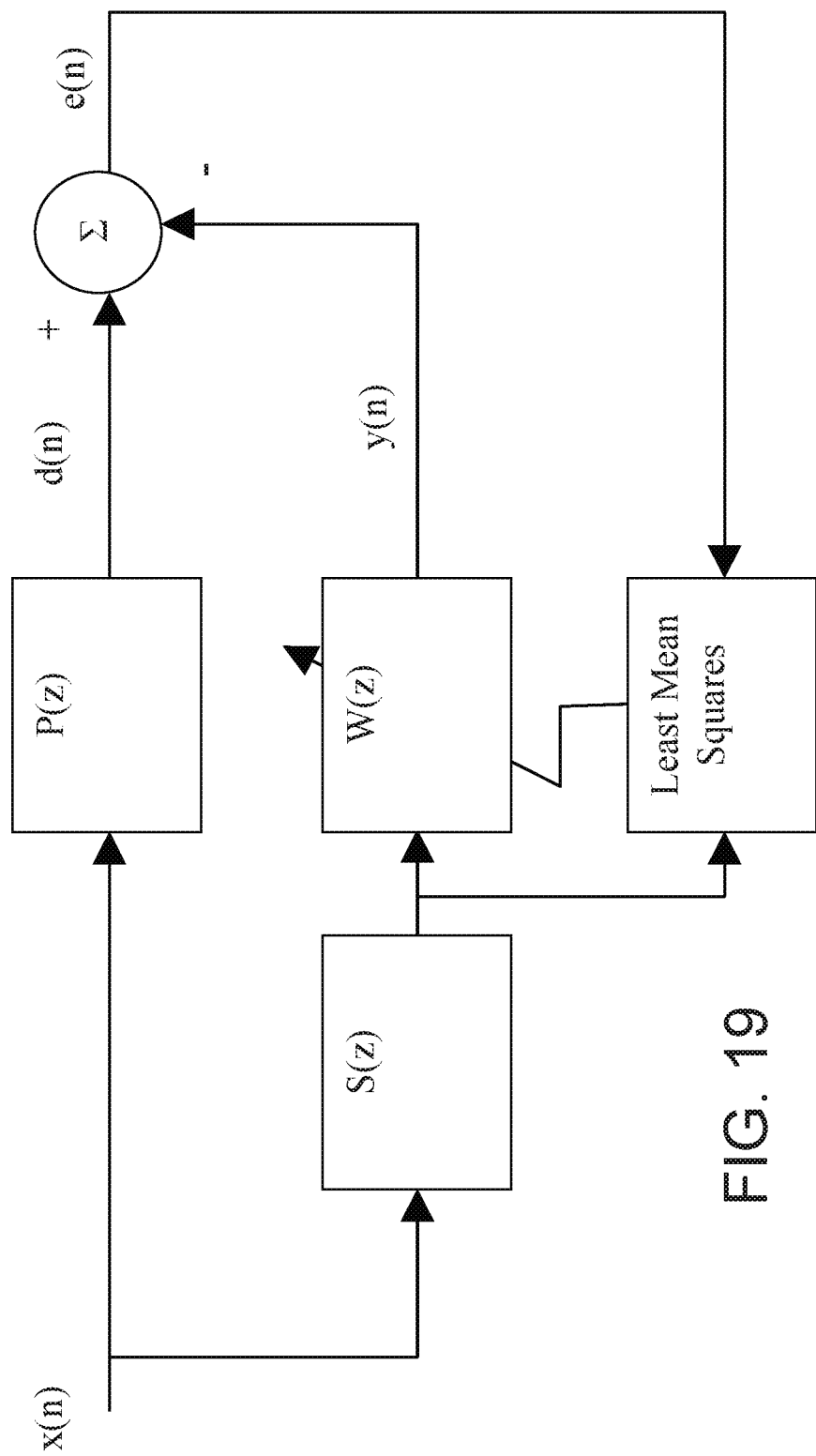
FIG. 19 is a block diagram of a filtered-X least mean squares (FXLMS ANC) algorithm.
Figure 20:
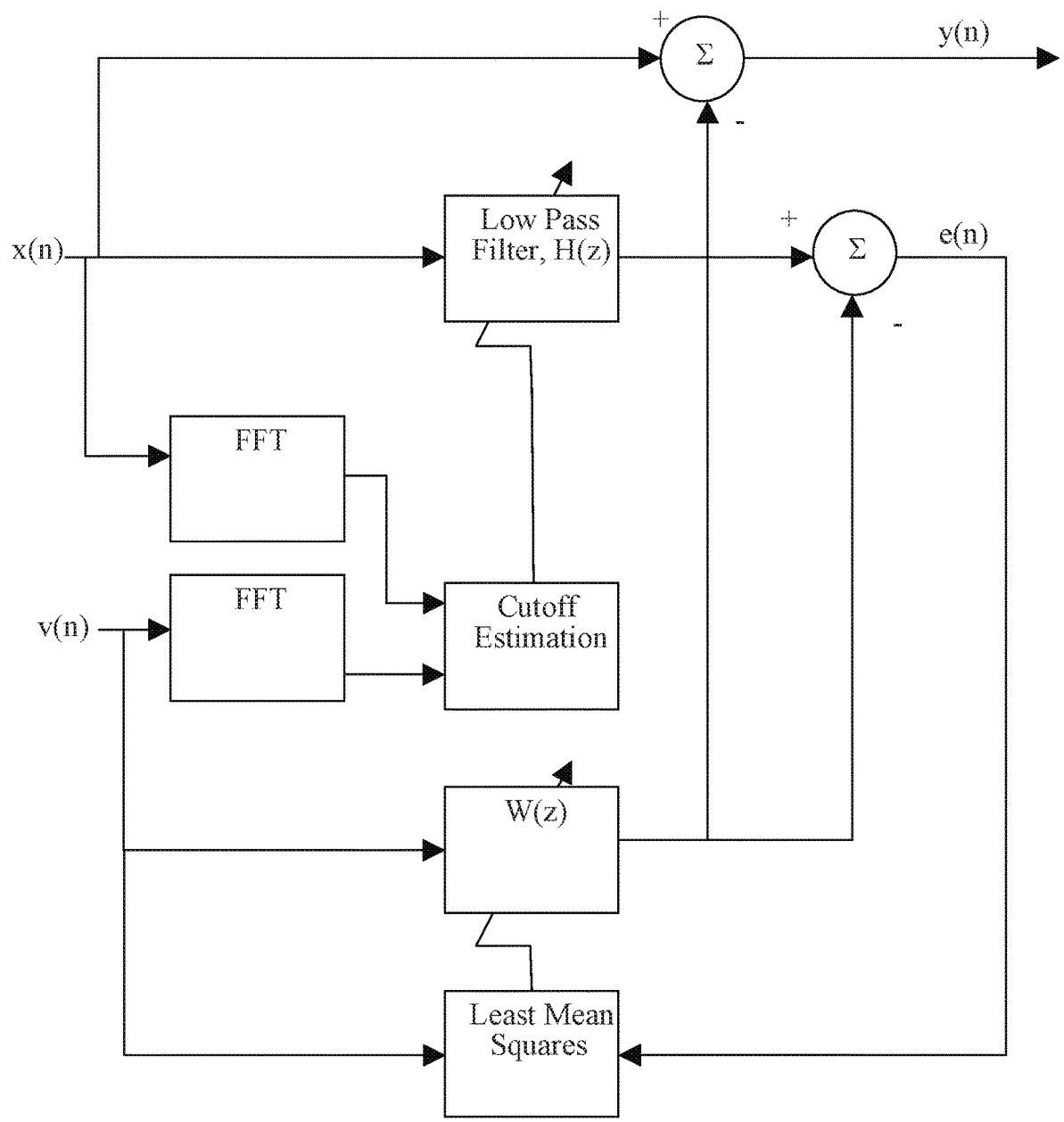
FIG. 20 is a block diagram of an implementation using the algorithm of FIG. 19.
Figure 21:
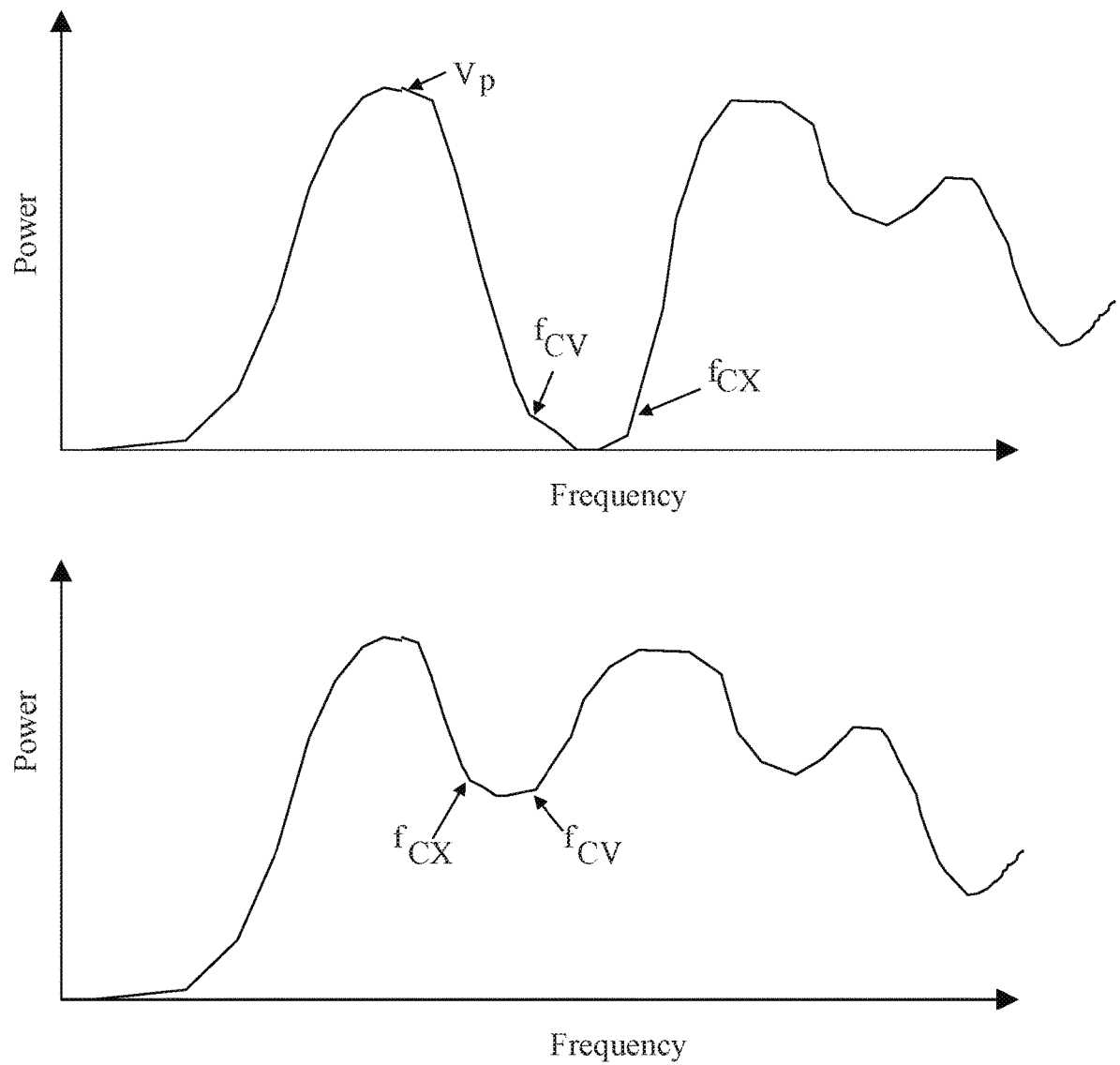
FIG. 21 shows two spectral power distributions related to the implementation of FIG. 20.

In a further implementation, more sophisticated signal processing methods may be used to minimize ECG artifacts induced by CPR chest compressions. For example, methods known as feed forward active noise cancellation (FANC) may be used. FIG. 19 shows a block diagram of the filtered-X least mean squares (FXLMS ANC) algorithm, as developed by Widrow and Burgess. P(z) represents the unknown plant through which the signal x(n) is filtered. Digital filter W(z) is adaptively adjusted to minimize the error signal e(n). In one implementation, as depicted in FIG. 20, x(n) is the unfiltered ECG signal, P(z) is eliminated from the diagram, and d(n) is approximated with the chest compression velocity signal v(n). In the LMS algorithm, assuming a mean square cost function $\xi(n)=E[e2(n)]$, the adaptive filter minimizes the instantaneous squared error, $\xi(n)=e2(n)$, using the steepest descent algorithm, which updates the coefficient vector in the negative gradient direction with step size μ:

$$w(n+1)=w(n)-\mu/2*\tilde{N}\xi(n),$$

where $\tilde{N}\xi(n)$ is an instantaneous estimate of the mean square error (MSE) gradient at time n equal to −2v(n) e(n). Stability and accuracy of the FXLMS ANC algorithm can be improved by adding a variable cutoff low pass filter H(z) to eliminate frequency components in the ECG not related to the chest compression artifact. In general, the spectral energy of the chest compression artifact is predominately lower than those of the ECG. A cutoff frequency of approximately 3 Hz is adequate in many cases, but this may vary from patient to patient and among different rescuers performing chest compressions. To overcome this difficulty, an FFT is performed on v(n) and input into a cutoff frequency estimation (CFE) procedure that determines the optimal cutoff frequency, fC, for the lowpass filter. In a preferred implementation, the decision is based on calculating the frequency, not to exceed 5 Hz, below which 80% of the waveform energy is present, but this percentage may vary and additional decision logic may be employed. For instance, an FFT may also be calculated for x(n), also input to the CFE procedure. By first normalizing amplitude of the frequency spectra X(z) amplitude peak of the compression artifact and then subtracting the velocity spectra V(z) from the normalized input X'(z), the difference spectra is calculated ΔX'(z)=X'(z)−V'(z). Frequencies are then determined for V(z) and ΔX'(z) at which most of the spectral energy is within, set in this embodiment to 97%, and labeled fCV and fCX, respectively, and shown in FIG. 21. FC is then set to the lesser of fCV and fCX. Alternatively, fC can be set to some intermediate frequency between fCV and fCX.

The quality of other physiological signals, such as impedance cardiographic (ICG), impedance pneumographic (IPG), or pulse oximetry, known to those skilled in the art, may also be be also be enhanced by the filter, particularly if the sensor is located on the thoracic cage in nearby proximity to the motion sensor from which the velocity signal is derived. Minimization of compression artifact with impedance pneumography signals can be accomplished with any of the previously described methods.

The adaptive filter can be used to minimize the cross-correlation of the adaptive-filter output with the reference signal or the cross-correlation of the adaptive-filter output with the measured ECG signal.

Many other implementations of the invention other than those described above are within the invention, which is defined by the following claims. For example, it is not necessary that the invention include an external defibrillator, as a device for assisting delivery of CPR could be provided without defibrillation capability. The CPR assistance device could even be a pocket device that is for assisting with manual delivery of CPR.

Features of the one aspect of the invention may not be required in implementations of other aspects of the invention. For example, it is not necessary in some implementations of the invention that chest compliance be determined, or that substantial release of the chest be determined, or that a particular type of sensor (e.g., accelerometer, force sensor, velocity sensor), or combination of sensors, be used, or that there be analysis of features of a motion waveform, or that maximum velocity be estimated, or that artifacts in detected ECG signals be reduced.

What is claimed is:

1. An apparatus for assisting a performance of chest compressions on a patient, the apparatus comprising:
    at least one pad or other structure configured to be applied near or at a location at which force is applied to produce chest compressions;
    at least one motion sensor coupled to the at least one pad or other structure for generating a motion signal during the chest compressions;
    at least one force sensor coupled to the at least one pad or structure for generating a force signal during the chest compressions;
    a feedback device configured to provide compression feedback during the performance of chest compressions; and
    processing circuitry configured to:
        receive and process the motion signal and the force signal during the chest compressions to determine a chest displacement parameter,
        determine the compression feedback based on the chest displacement parameter, and
        generate an output signal for the feedback device to provide the determined compression feedback.

2. The apparatus of claim 1, wherein the at least one motion sensor comprises a conductor and a magnet.

3. The apparatus of claim 1, wherein the at least one pad or other structure is configured to be adhered to the patient's skin.

4. The apparatus of claim 1, wherein the at least one pad or other structure comprises an electrically conductive material configured to deliver defibrillation current to the patient.

5. The apparatus of claim 4, wherein the at least one pad or other structure comprises an adhesive conductive gel coupling agent adhered to the electrically conductive material.

6. The apparatus of claim 1, wherein the at least one pad or other structure comprises an electrically insulating material.

7. The apparatus of claim 1, wherein the at least one motion sensor is configured to sense a motion due to an anterior surface of the thorax or a posterior surface of the thorax.

8. The apparatus of claim 1, wherein the processing circuitry is configured to determine chest compliance based on the motion signal and the force signal during the chest compressions.

9. The apparatus of claim 1, wherein the processing circuitry is configured to determine compression depth based on the motion signal during the chest compressions.

10. The apparatus of claim 9, wherein the output signal comprises a prompt for the rescuer as to whether compressions are within desired limits of compression depth or outside desired limits of compression depth.

11. The apparatus of claim 9, wherein the output signal comprises a prompt for the rescuer as to whether compressions are outside desired limits of compression depth.

12. The apparatus of claim 11, wherein the prompt comprises at least one of: a visual and an audible message to the rescuer.

13. The apparatus of claim 1, wherein the processing circuitry is configured to acquire and analyze ECG signals from the patient for performing rhythm analysis.

14. The apparatus of claim 13, wherein the processing circuitry is configured to filter the ECG signals to remove chest compression artifacts.

15. The apparatus of claim 13, wherein the processing circuitry is configured to generate a trigger to deliver a defibrillatory shock to the patient.

16. The apparatus of claim 1, wherein the at least one motion sensor comprises an accelerometer.

17. The apparatus of claim 1, wherein the processing circuitry is configured to determine chest compliance based on the motion signal relative to the force signal during the performance of the chest compressions.

18. The apparatus of claim 17, wherein the output signal comprises a prompt for the rescuer to adjust to the chest compressions based on the chest compliance.

19. The system of claim 1, wherein the chest displacement parameter comprises a chest release displacement point.

20. The system of claim 1, wherein generating the output signal comprises a prompt for the rescuer to adjust to the chest compressions based on the chest compliance.

21. The system of claim 1, wherein generating the output signal for the feedback device is based on a comparison of the chest displacement parameter to a threshold.

22. The system of claim 1, wherein the chest displacement parameter comprises a relative motion relative to a location of the patient's thorax.

23. The system of claim 1, wherein the chest displacement parameter comprises an acceleration signal decomposed into a plurality of triangles to determine amplitude ratios.

24. A system for assisting a performance of chest compressions on a patient, the system comprising:
   an external defibrillator configured to deliver at least one defibrillatory shock to the patient;
   at least one pad or other structure configured to be connected to the external defibrillator and configured to be applied near or at a location at which force is applied to produce chest compressions;
   at least one sensor coupled to the at least one pad or other structure for generating a motion signal during the chest compressions;
   a force sensor coupled to the at least one pad or structure for generating a force signal during the chest compressions; and
   processing circuitry configured to:
      receive and process the motion signal and the force signal during the chest compressions to determine a chest displacement parameter, and
      generate an output signal for the external defibrillator based on the chest displacement parameter.

25. The system of claim 24, wherein the at least one sensor comprises an accelerometer powered by the external defibrillator.

26. The system of claim 24, wherein the processing circuitry is comprised within the external defibrillator.

27. The system of claim 24, wherein the external defibrillator is configured to prompt the rescuer as to whether compressions are within desired limits of compression depth.

28. The system of claim 24, wherein the external defibrillator is configured to prompt the rescuer as to whether compressions are outside desired limits of compression depth.

29. The system of claim 24, wherein the at least one pad or other structure is configured to be placed on anterior of thorax, and a second pad or other structure configured to be placed on posterior of thorax.

30. The system of claim 24, wherein the at least one pad or other structure comprises an electrically conductive material configured to deliver defibrillation current to the patient.

31. The system of claim 30, wherein the at least one pad or other structure comprises an adhesive conductive gel coupling agent adhered to the electrically conductive material.

32. The system of claim 24, wherein the at least one pad or other structure comprises an electrically insulating material.

* * * * *